US009098743B2

(12) United States Patent
Ishida et al.

(10) Patent No.: US 9,098,743 B2
(45) Date of Patent: Aug. 4, 2015

(54) FUNDUS IMAGE PROCESSING APPARATUS, FUNDUS IMAGE PROCESSING METHOD, AND RECORDING MEDIUM

(71) Applicants: NIDEK CO., LTD., Aichi (JP); NATIONAL UNIVERSITY CORPORATION HOKKAIDO UNIVERSITY, Sapporo-shi, Hokkaido (JP)

(72) Inventors: Susumu Ishida, Sapporo (JP); Kousuke Noda, Sapporo (JP); Michiyuki Saito, Sapporo (JP); Masahiko Kobayashi, Aichi (JP); Yasuhiro Hoshikawa, Aichi (JP)

(73) Assignees: NATIONAL UNIVERSITY CORPORATION HOKKAIDO UNIVERSITY, Hokkaido (JP); NIDEK CO., LTD., Aichi (JP)

( * ) Notice: Subject to any disclaimer, the term of this patent is extended or adjusted under 35 U.S.C. 154(b) by 0 days.

(21) Appl. No.: 14/228,466

(22) Filed: Mar. 28, 2014

(65) Prior Publication Data

US 2014/0294235 A1 Oct. 2, 2014

(30) Foreign Application Priority Data

Mar. 29, 2013 (JP) ................................ 2013-070790

(51) Int. Cl.
*G06K 9/00* (2006.01)
*A61B 3/00* (2006.01)

(52) U.S. Cl.
CPC ........... *G06K 9/0061* (2013.01); *A61B 3/0025* (2013.01)

(58) Field of Classification Search
CPC .... A61B 3/0025; A61B 3/12; A61B 5/14555; A61B 3/1241; A61B 5/0275; G06K 9/0061; G01N 21/86
See application file for complete search history.

(56) References Cited

U.S. PATENT DOCUMENTS 5,308,919 A * 5/1994 Minnich ...................... 600/320
8,355,544 B2 * 1/2013 Gomez-Ulla de Irazazabal et al. ............................ 382/117
8,687,862 B2 * 4/2014 Hsu et al. ...................... 382/128
8,787,638 B2 * 7/2014 Zee et al. ...................... 382/128
2012/0236259 A1 * 9/2012 Abramoff et al. ............ 351/206

FOREIGN PATENT DOCUMENTS

JP 10-243924 9/1998

* cited by examiner

*Primary Examiner* — Tom Y Lu
(74) *Attorney, Agent, or Firm* — Rankin, Hill & Clark LLP

(57) ABSTRACT

A fundus image processing apparatus that processes a fundus image of an examinee's eye, the fundus image processing apparatus includes: a processor; and a memory storing computer readable instructions, when executed by the processor, causing the fundus image processing apparatus to: identify the optic disc included in the fundus image; identify a blood vessel included in the fundus image; calculate an upper diameter ratio which is a diameter ratio of those of the identified blood vessels that are positioned in a region above a height of the optic disc; calculate a lower diameter ratio which is a diameter ratio of those of the identified blood vessels that are positioned in a region under the height of the optic disc; and calculate an arteriovenous diameter ratio in the fundus of the examinee's eye based on the upper diameter ratio and the lower diameter ratio.

13 Claims, 13 Drawing Sheets

FUNDUS IMAGE PROCESS
S1 ACQUIRE FUNDUS IMAGE
S2 IMAGE PREPROCESSING
S3 ACQUIRE G-VALUE IMAGE
S4 G-VALUE LUMINANCE DIFFERENCE IMAGE ACQUISITION PROCESS
S5 OPTIC DISC DETECTION PROCESS
S6 BLOOD VESSEL DETECTION PROCESS
S7 ARTERIOVENOUS DIAMETER RATIO CALCULATION PROCESS
END

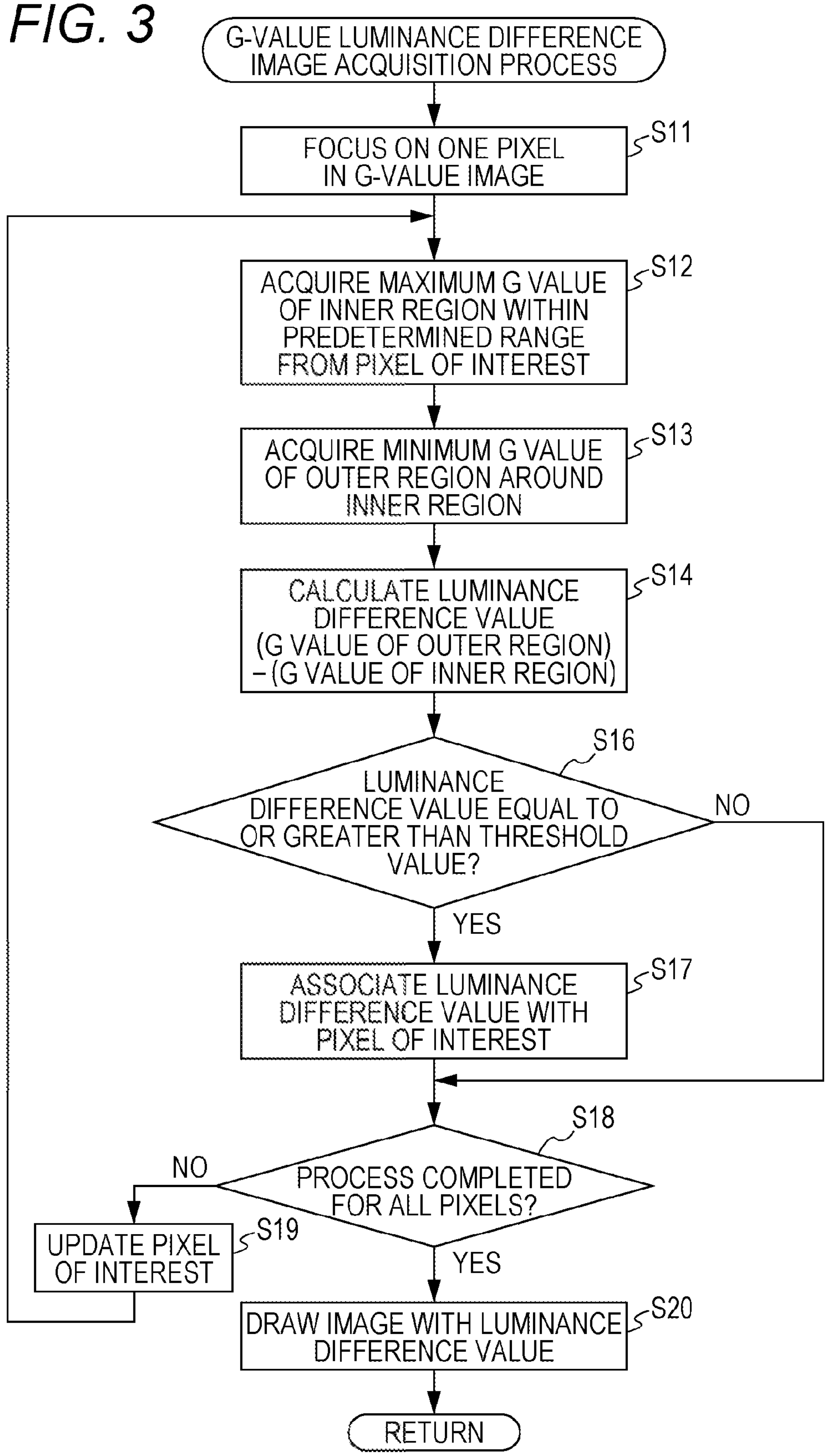
FIG. 3
G-VALUE LUMINANCE DIFFERENCE IMAGE ACQUISITION PROCESS
S11
FOCUS ON ONE PIXEL IN G-VALUE IMAGE
S12
ACQUIRE MAXIMUM G VALUE OF INNER REGION WITHIN PREDETERMINED RANGE FROM PIXEL OF INTEREST
S13
ACQUIRE MINIMUM G VALUE OF OUTER REGION AROUND INNER REGION
S14
CALCULATE LUMINANCE DIFFERENCE VALUE (G VALUE OF OUTER REGION) −(G VALUE OF INNER REGION)
S16
LUMINANCE DIFFERENCE VALUE EQUAL TO OR GREATER THAN THRESHOLD VALUE?
NO
YES
S17
ASSOCIATE LUMINANCE DIFFERENCE VALUE WITH PIXEL OF INTEREST
S18
PROCESS COMPLETED FOR ALL PIXELS?
NO
YES
S19
UPDATE PIXEL OF INTEREST
S20
DRAW IMAGE WITH LUMINANCE DIFFERENCE VALUE
RETURN

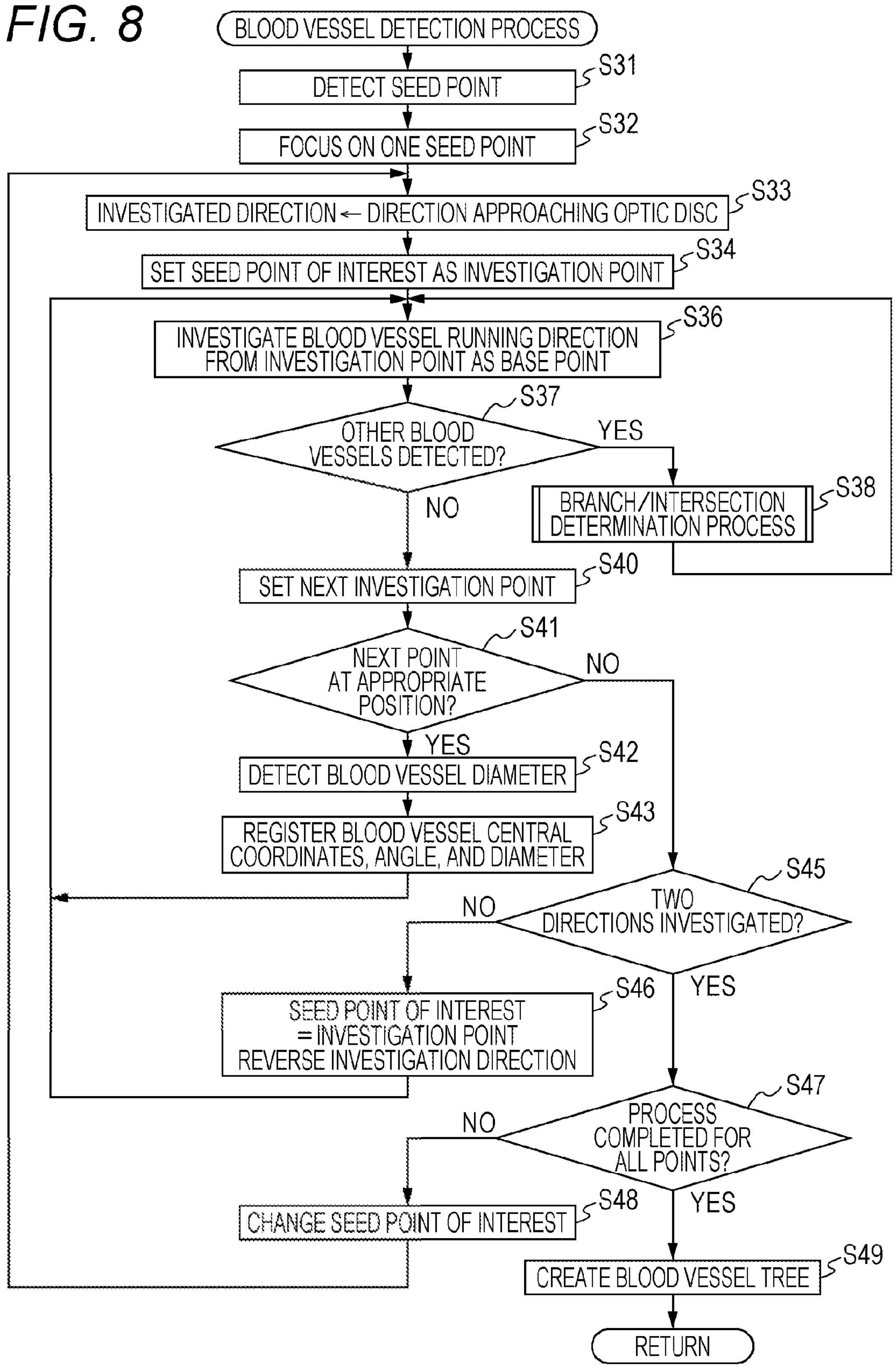
FIG. 8
BLOOD VESSEL DETECTION PROCESS
DETECT SEED POINT
S31
FOCUS ON ONE SEED POINT
S32
INVESTIGATED DIRECTION ← DIRECTION APPROACHING OPTIC DISC
S33
SET SEED POINT OF INTEREST AS INVESTIGATION POINT
S34
INVESTIGATE BLOOD VESSEL RUNNING DIRECTION FROM INVESTIGATION POINT AS BASE POINT
S36
OTHER BLOOD VESSELS DETECTED?
S37
YES
NO
BRANCH/INTERSECTION DETERMINATION PROCESS
S38
SET NEXT INVESTIGATION POINT
S40
NEXT POINT AT APPROPRIATE POSITION?
S41
NO
YES
DETECT BLOOD VESSEL DIAMETER
S42
REGISTER BLOOD VESSEL CENTRAL COORDINATES, ANGLE, AND DIAMETER
S43
TWO DIRECTIONS INVESTIGATED?
S45
NO
YES
SEED POINT OF INTEREST = INVESTIGATION POINT REVERSE INVESTIGATION DIRECTION
S46
PROCESS COMPLETED FOR ALL POINTS?
S47
NO
YES
CHANGE SEED POINT OF INTEREST
S48
CREATE BLOOD VESSEL TREE
S49
RETURN

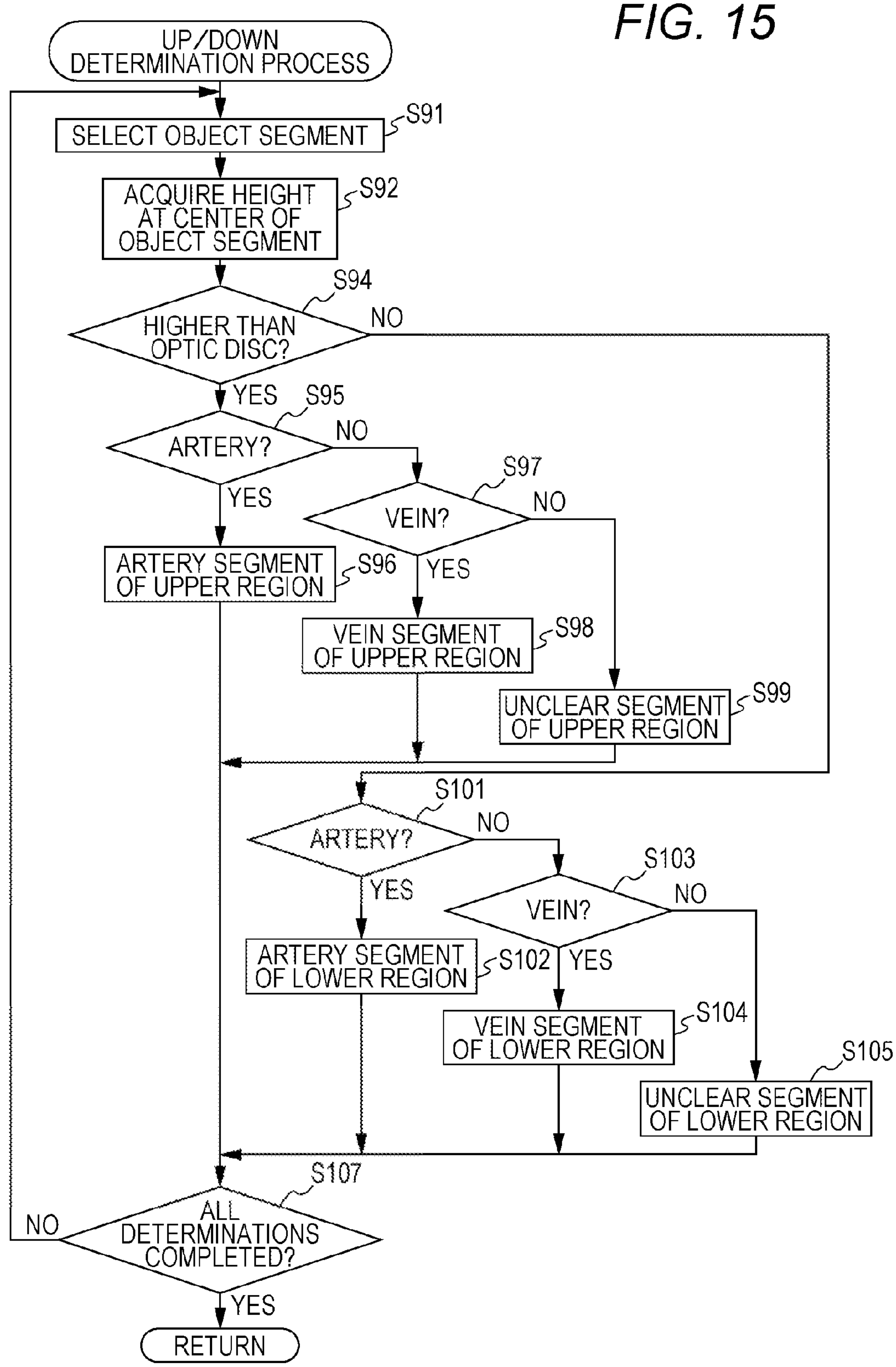
FIG. 15
UP/DOWN DETERMINATION PROCESS
SELECT OBJECT SEGMENT
S91
ACQUIRE HEIGHT AT CENTER OF OBJECT SEGMENT
S92
S94
HIGHER THAN OPTIC DISC?
NO
YES
S95
ARTERY?
NO
YES
S97
VEIN?
NO
ARTERY SEGMENT OF UPPER REGION
S96
YES
VEIN SEGMENT OF UPPER REGION
S98
UNCLEAR SEGMENT OF UPPER REGION
S99
S101
ARTERY?
NO
YES
S103
VEIN?
NO
ARTERY SEGMENT OF LOWER REGION
S102
YES
VEIN SEGMENT OF LOWER REGION
S104
S105
UNCLEAR SEGMENT OF LOWER REGION
S107
NO
ALL DETERMINATIONS COMPLETED?
YES
RETURN

FUNDUS IMAGE PROCESSING APPARATUS, FUNDUS IMAGE PROCESSING METHOD, AND RECORDING MEDIUM

CROSS-REFERENCE TO RELATED APPLICATION

This application is based upon and claims the benefit of priority of Japanese Patent Application No. 2013-070790 filed on Mar. 29, 2013, the contents of which are incorporated herein by reference in its entirety.

BACKGROUND

1. Technical Field

The present disclosure relates to a fundus image processing apparatus, a fundus image processing method, and a recording medium with a fundus image processing program recorded therein.

2. Related Art

There is a known technique for processing a fundus image of an examinee's eye to calculate the ratio of the diameter of the artery and the diameter of the vein in the fundus (hereafter referred to as the "arteriovenous diameter ratio"). For example, JP-A-10-243924 discusses a method for measuring an arteriovenous diameter ratio. The method sets a plurality of regions $R_n$ enclosed by two concentric circles with different radii with reference to the center of the optic nerve papilla (hereafter simply referred to as the "optic disc"). Within the set regions $R_n$ a plurality of blood vessels is extracted. From the extracted plurality of blood vessels, two blood vessels with a small distance between the blood vessels are selected as a blood vessel pair. From the selected blood vessel pair, the arteriovenous diameter ratio is calculated.

SUMMARY

A fundus image processing apparatus that processes a fundus image of an examinee's eye, the fundus image processing apparatus includes: it processor; and a memory storing computer readable instructions, when executed by the processor, causing the fundus image processing apparatus to: identify the optic disc included in the fundus image; identify a blood vessel included in the fundus image; calculate an upper diameter ratio which is a diameter ratio of those of the identified blood vessels that are positioned in a region above a height of the optic disc; calculate a lower diameter ratio which is a diameter ratio of those of the identified blood vessels that are positioned in a region under the height of the optic disc; and calculate an arteriovenous diameter ratio in the fundus of the examinee's eye based on the upper diameter ratio and the lower diameter ratio.

BRIEF DESCRIPTION OF DRAWINGS

FIG. 3 is a flowchart of a G-value luminance difference image acquisition process performed in the fundus image process;

FIG. 8 is a flowchart of a blood vessel detection process performed in the fundus image process;

FIG. 15 is a flow chart of an up/down determination process performed in the arteriovenous diameter ratio calculation process.

DETAILED DESCRIPTION

Figure 1:
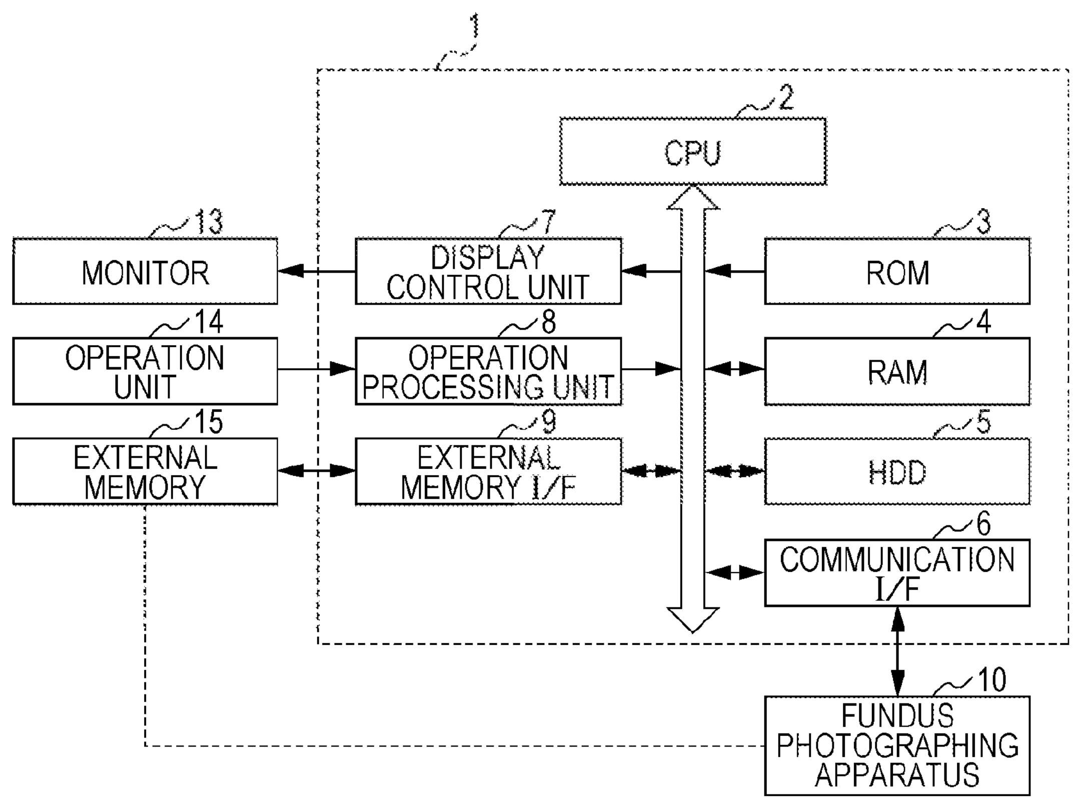
FIG. 1 is a block diagram illustrating an electrical configuration of a personal computer (PC) of a fundus image processing apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The conventional technique calculates the arteriovenous diameter ratio without sufficiently considering the characteristics of the blood vessels in the fundus. As a result, the arteriovenous diameter ratio useful for diagnosis may not be accurately calculated.

An object of the present disclosure is to provide a fundus image processing apparatus, a fundus image processing method, and a recording medium with a fundus image processing program recorded therein for calculating the anteriovenous diameter ratio with increased accuracy.

An aspect of the present disclosure provides the following arrangements:

a fundus image processing apparatus that processes a fundus image of an examinee's eye, the fundus image processing apparatus includes: a processor; and a memory storing computer readable instructions, when executed by the processor, causing the fundus image processing apparatus to: identify the optic disc included in the fundus image; identify a blood vessel included in the fundus image; calculate an upper diameter ratio which is a diameter ratio of those of the identified blood vessels that are positioned in a region above a height of the optic disc; calculate a lower diameter ratio which is a diameter ratio of those of the identified blood vessels that are positioned in a region under the height of the optic disc; and calculate an arteriovenous diameter ratio in the fundus of the examinee's eye based on the upper diameter ratio and the lower diameter ratio;

a non-transitory computer readable recording medium stores computer readable instructions, when executed by the processor, causing an image processing apparatus to: identify the optic disc included in the fundus image; identify a blood vessel included in the fundus image; calculate an upper diameter ratio which is a diameter ratio of those of identified the blood vessels that are positioned in a region above a height of the optic disc; calculate a lower diameter ratio which is a diameter ratio of those of the identified blood vessels that are positioned in a region wider the height of the optic disc; and calculate an arteriovenous diameter ratio in the fundus of the examinee's eye based on the upper diameter ratio and the lower diameter ratio; and a fundus image processing method for processing a fundus image of an examinee's eye, the fundus image processing method comprising: identifying the optic disc included in the fundus image; identifying a blood vessel included in the fundus image; calculating an upper diameter ratio which is a diameter ratio of those of the identified blood vessels that are positioned in a region above a height of the optic disc; calculate a lower diameter ratio which is a diameter ratio of those of the identified blood vessels that are positioned in a region under the height of the optic disc; and calculating an arteriovenous diameter ratio in the fundus of the examinee's eye based on the upper diameter ratio and the lower diameter ratio.

A fundus image processing apparatus according to the technology of the present disclosure can calculate the arteriovenous diameter ratio with increased accuracy.

In the following, an exemplary embodiment will be described. First, a schematic configuration of a personal computer (hereafter referred to as a "PC") 1 as a fundus image processing apparatus according to the present embodiment will be described with reference to FIG. 1.

In the present embodiment, a fundus photographing apparatus 10 for photographing a fundus image and the PC 1 for processing the fundus image are independent apparatuses. The fundus photographing apparatus 10 photographs a fundus image. The PC 1 acquires the photographed fundus image via at least one of a network, an external memory, and the like, and then processes the acquired fundus image.

The fundus image processing apparatus is not limited to the PC 1. Alternatively, for example, the fundus photographing apparatus 10 may by itself photograph and process the fundus image. In this case, the fundus photographing apparatus 10 acts as a fundus image processing apparatus.

As illustrated in FIG. 1, the PC 1 is provided with a central processing unit (CPU) (processor) 2 for controlling the PC 1. To the CPU 2, a read only memory (ROM) 3, a random access memory (RAM) 4, a hard disk drive (HDD) 5, a communication interface (I/F) 6, a display control unit 7, an operating process unit 8, and an external memory I/F 9 are connected via a bus.

In the ROM 3, a program executed by the CPU 2, such as a basic input output system (BIOS), is stored. The RAM 4 temporarily stores various kinds of information. The HDD 5 is a non-transitory storage medium that can retain the stored contents even when power supply is turned off. As the non-transitory storage medium, instead of the HDD 5, other storage media, such as a flash ROM, may be used. The HDD 5 stores a fundus image processing program for processing the fundus image. In the present embodiment, as will be described below, the stored fundus image processing program specifically includes an arteriovenous ratio calculation program for executing an arteriovenous ratio calculation process, an optic disc detection program for executing an optic disc detection process, and a blood vessel detection program for executing a blood vessel detection process.

The display control unit 7 controls the display on a monitor 13. The operating unit 14 receives various operations input by a user on the PC 1. The operating unit 14 includes, for example, a keyboard and a mouse. The operating process unit 8 is connected to the operating unit 14 and detects the operation inputs on the operating unit 14. In the present embodiment, the monitor 13 and the operating unit 14 are externally installed. However, at least one of the monitor 13 and the operating unit 14 may be incorporated into the PC 1.

The PC 1 is connected to an external device, such as the fundus photographing apparatus 10, via the communication I/F 6. The PC 1 of the present embodiment is configured to acquire data of the fundus image photographed by the fundus photographing apparatus 10 via the communication I/F 6. The external memory 15 is connected to the PC 1 via the external memory I/F 9. The external memory 15 may include various storage media, such as a universal serial bus (USB) memory and a compact disc read only memory (CD-ROM). In the present embodiment, the PC 1 may acquire the data of the fundus image photographed by the fundus photographing apparatus 10 via the external memory 15. For example, the user attaches the external memory 15 to the fundus photographing apparatus 10, and stores the data of the fundus image photographed by the fundus photographing apparatus 10 in the external memory 15. Then, the user attaches the external memory 15 removed from the fundus photographing apparatus 10 onto the PC 1, and has the PC 1 read the data of the fundus image stored in the external memory 15. As a result, the data of the fundus image is acquired by the PC 1.

As the fundus photographing apparatus (fundus image photographing apparatus) 10, various devices that can photograph the fundus image may be used. In the present embodiment, for example, a known fundus camera configured to illuminate and photograph the fundus through the pupil is used as the fundus photographing apparatus 10. However, a stereoscopic fundus camera, an ophthalmic scanning laser ophthalmoscope (SLO), an optical coherence tomography (OCT), a slit-lamp microscope, or the like may be used as the fundus photographing apparatus 10. The stereoscopic fundus camera photographs a single fundus from as plurality of directions corresponding to different parallaxes. The SLO acquires a fundus image by scanning the fundus with illuminating light and receiving reflected light of the illuminating light reflected by the fundus. The main functions of the OCT include acquiring an interference signal between the illuminating light reflected by the fundus and reference light, and obtaining a tomographic image of the fundus from the acquired interference signal. It is also possible to acquire a two-dimensional image of the fundus by processing the interference signal acquired by the OCT.

Figure 2:
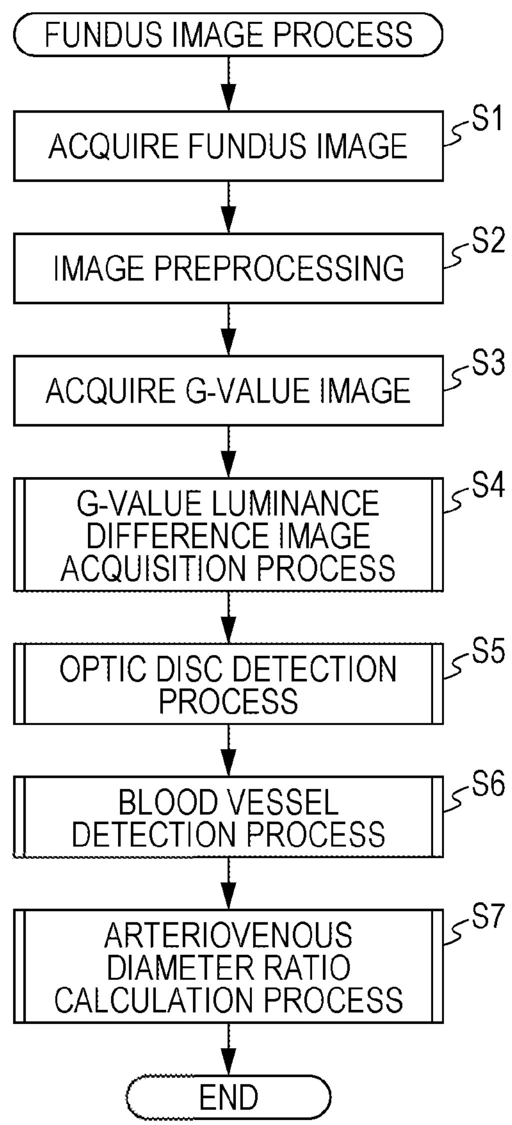
FIG. 2 is a flowchart of a fundus image process performed by the PC.
Figure 4:
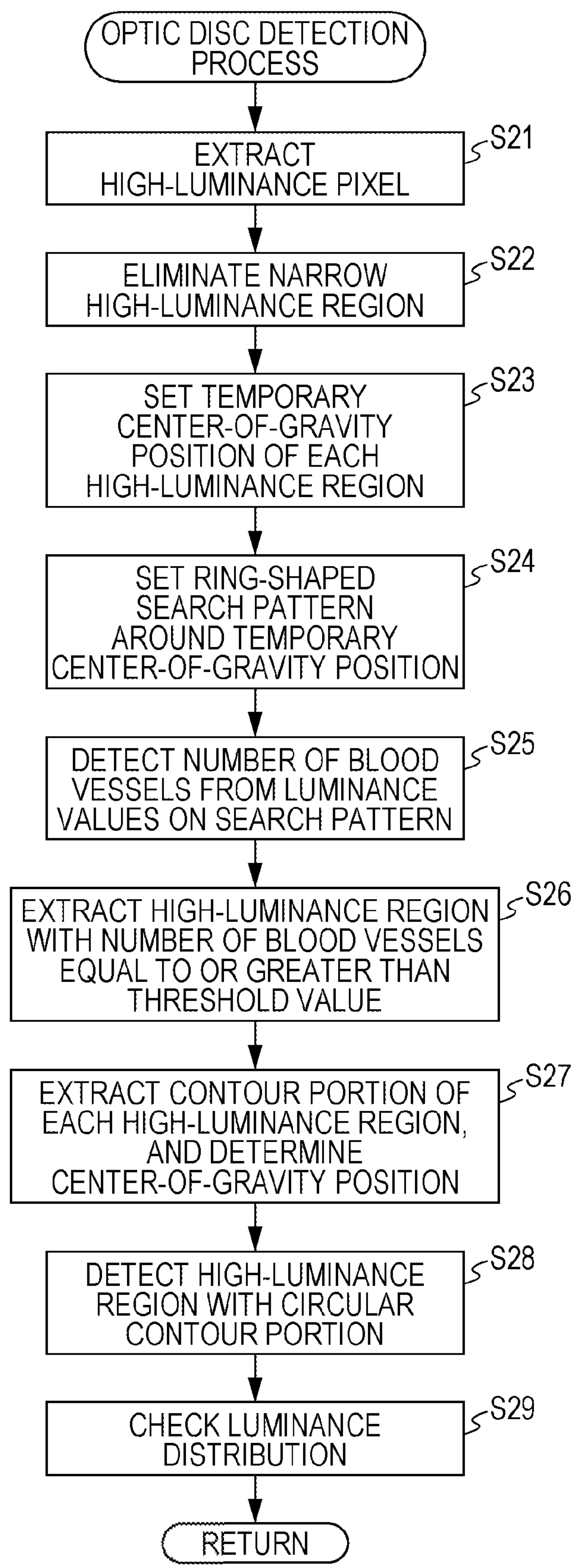
FIG. 4 is a flowchart of an optic disc detection process performed in the fundus image process.

With reference to FIGS. 2 to 16, a fundus image process according to the present embodiment will be described. As illustrated in FIG. 2, the fundus image process according to the present embodiment includes an optic disc detection process (Step S5), a blood vessel detection process (Step S6), and an arteriovenous diameter ratio calculation process (Step S7). The optic disc detection process (Step S5) is a process of detecting the optic disc included in the fundus image. The blood vessel detection process (Step S6) is a process of detecting blood vessels included in the fundus image. The arteriovenous diameter ratio calculation process (Step S7) is a process of calculating the ratio of the diameter of an artery and the diameter of a vein included in the fundus image.

The processes described below are merely exemplary. Thus, the processes may be modified by addition, alteration, or omission of a process. For example, in the arteriovenous diameter ratio calculation process (Step S7) according to the present embodiment, the arteriovenous diameter ratio of blood vessels in the fundus is calculated based on the result of detection of the optic disc by the optic disc detection process (Step S5) and the result of detection of blood vessels by the blood vessel detection process (Step S6). However, the CPU 2 of the PC 1 may not perform all of S5 to S7. More specifically, the CPU 2 may be configured to detect the optic disc and blood vessels included in the fundus image without executing at least one of the optic disc detection process and the blood vessel detection process. The CPU 2 is configured to execute the arteriovenous ratio calculation process by using the detection results. In this case, the CPU 2 may be configured to let the user designate the positions of the optic disc and a blood vessel in the fundus image by operating the operating unit 14. Further, the CPU 2 may identify the designated positions as the positions of the optic disc and the blood vessel. The CPU 2 may detect the positions of the optic disc and the blood vessel by using a separate algorithm, and identify the detected positions as the positions of the optic disc and the blood vessel.

As described above, in the HDD 5 of the PC 1, the fundus image processing program for controlling the fundus image process is stored. The user inputs an instruction for executing the fundus image process on the operating unit 14 or the external device. The CPU 2 then executes the fundus image process illustrated in FIG. 2 in accordance with the fundus image processing program.

As illustrated in FIG. 2, at the start of the fundus image process, the data of the fundus image of the examinee's eye is acquired, and a fundus image is expanded in the RAM 4 (Step S1). As described above, in the present embodiment, the PC 1 may acquire the data of the fundus image from the fundus photographing apparatus 10 via the communication I/F 6 or the external memory I/F 9. The data of the fundus image may be stored in the HDD 5 in advance before the fundus image process is executed. In this case, in the process of Step S1, the PC 1 may acquire the data of the fundus image from the HDD 5.

In present embodiment, the data of the fundus image is represented in 256 gradation levels according to RGB format. Light of green (G) and blue (B) is absorbed by blood vessels more readily than light of red (R). Thus, the blood vessel detection process (Step S6) employs, for example, at least one of the values of green (G) and blue (B). In this was compared with the use of the value of red (R), the accuracy of detection of the blood vessel is increased. However, the PC 1 is not limited to use the above data. Alternatively, to execute the calculation of arteriovenous diameter ratio or the like, the PC 1 may use an image that enables the PC 1 to distinguish the blood vessel from other regions.

In order to simplify the subsequent processes, the PC 1 executes preprocessing on the acquired fundus image (Step S2). For example, in the present embodiment, the preprocessing involves removal of noise with a known median filter. A masking process is performed to distinguish the inside from outside of an image region. Further, pixel values are optimized by processing a pixel value histogram. The concrete contents of the preprocessing of the fundus image may be modified as needed. Alternatively, the preprocessing may be omitted.

From the data of the fundus image acquired in Step S1, data of a G-value image is acquired (Step S3). The G-value image refers to as fundus image represented only by G values indicating the color of green. In the present embodiment, in Step S1, the fundus image of RGB format is already acquired. Thus, the CPU 2 may acquire the data of the G-value image by acquiring only the G values from the data of the fundus image of RGB format. Thereafter, a G-value luminance difference image acquisition process (Step S4), the optic disc detection process (Step S5), the blood vessel detection process (Step S6), and the arteriovenous diameter ratio calculation process (Step S7) are executed successively, and then the fundus image process ends. In the following, the processes of Step S4 to Step S7 will be described in detail.

Referring to FIG. 3, the G-value luminance difference image acquisition process (Step S4) will be described. A G-value luminance difference image refers to an image represented by a luminance difference between an inner region in the vicinity of a pixel of interest and an outer region around the inner region. First, one of a plurality of pixels constituting the G-value image is designated as a pixel of interest (Step S11). Then, a maximum value of the G values in a region ("inner region") within a predetermined range from the pixel of interest is acquired (Step S12). In the present embodiment, the inner region corresponds to a region of pixels located within a predetermined distance (in the present embodiment, for example, a distance corresponding to one pixel) in directions of 0 degree (in the positive direction of the X axis), 45 degrees, 90 degrees (in the positive direction of the Y axis), 135 degrees, 180 degrees (in the negative direction of the X axis), 225 degrees, 270 degrees (the negative direction of the Y axis), and 315 degrees from the pixel of interest (i.e., with respect to the pixel of interest). Thus, in the present embodiment, the inner region has, for example, a rectangular shape.

Then, a maximum value of the G values in a region (hereinafter, referred to as an "outer region") disposed around the inner region is acquired (Step S13). In the present embodiment, the outer region corresponds to a region of pixels that are positioned in the directions of 0 degrees, 45 degrees, 90 degrees, 135 degrees, 180 degrees, 225 degrees, 270 degrees, and 315 degrees from the pixel of interest (i.e., with respect to the pixel of interest), which are located within a predetermined range of distance (in the present embodiment, for example, a distance corresponding to 3 to 10 pixels) from the pixel of interest. Thus, in the present embodiment, the outer region has a radial shape. The shapes and ranges of the inner region and the outer region may be modified as needed.

The CPU 2 calculates the luminance difference value by subtracting the maximum value of the G values in the inner region from the maximum value of the G values in the outer region (Step S14). As described above, the colors of green (G) and blue (B) are absorbed by blood vessels more readily than the color of red (R). As a result, in the G-value image and the B-value image, the values of the pixels in a blood vessel (G values or B values) are lower than the values of the pixels outside the blood vessel. Thus, when the inner region is in the blood vessel, the maximum value of the pixel values in the inner region becomes lower than the maximum value of the pixel values in the outer region including a region outside the blood vessel. The inner region and the outer region may both include a region outside the blood vessel. In this case, the difference between the maximum value of the pixel values in the inner region and the maximum value of the pixel values in the outer region becomes smaller than when the inner region is within the blood vessel.

The above property is utilized by the CPU 2 in acquiring the G-value luminance difference image that clearly shows the blood vessel. Specifically, the CPU 2 determines whether the luminance difference value calculated in Step S14 is equal to or greater than a threshold value (Step S16). The threshold value may be a predetermined fixed value, or a value set by the user. When the luminance difference value is equal to or greater than the threshold value, the CPU 2 stores the luminance difference value calculated in Step S14 in the RAM 4, for example, in association with the pixel of interest. Thus, the CPU 2 associates the luminance difference value with the pixel of interest (Step S17). When the luminance difference value is less than the threshold value (Step S16: NO), the process goes onto a determination in Step S18.

Then, the CPU 2 determines whether the process has been completed for all of the pixels constituting the G-value image (Step S18). When there are pixels still to be processed as a pixel of interest (Step S18: NO), the CPU 2 designates one of the unprocessed pixels as a pixel of interest (Step S19), and the process returns to Step S12. When the process has been completed for all of the pixels (Step S18: YES), an image is drawn with the luminance difference values stored in Step S17. Thus, the G-value luminance difference image is acquired (Step S20). Thereafter, the process returns to the fundus image process (see FIG. 2), and proceeds to the optic disc detection process (Step S5). In the acquired G-value luminance difference image, the difference in luminance between the pixels inside the blood vessel and the pixels outside the blood vessel is clearly exhibited. For example, the CPU 2 uses the G-value luminance difference image in a blood vessel detection process (see FIG. 8) as will be described below. Accordingly, the CPU 2 can detect the blood vessel with increased accuracy. Alternatively, as described above, the CPU 2 may be configured to perform the process without acquiring the G-value image, the B-value image, and the G-value luminance difference image. Further, the CPU 2 may acquire the B-value luminance difference image in the same procedure as in the G-value luminance difference image acquisition process.

Referring to FIGS. 4 to 7, the optic disc detection process will be described. Generally, the luminance of the optic disc region is higher than the luminance in other regions of the fundus. Thus, in the optic disc detection process, the optic disc is detected based on the luminance of the fundus image. However, in the fundus, it is not always the case that the luminance of only the optic disc region is high relative to the luminance of other regions. There are other cases, for example, the fundus may have a vitiligo due to a lesion or the like, or the fundus image may include noise or a flare due to the optical system. In these cases, the luminance of one region may be increased relative to the luminance of another region. Therefore, it is desirable to distinguish the optic disc from vitiligo and the like. In the present embodiment, the optic disc detection process distinguishes the optic disc from vitiligo and the like so as to increase the accuracy of detection of the optic disc.

Figure 5:
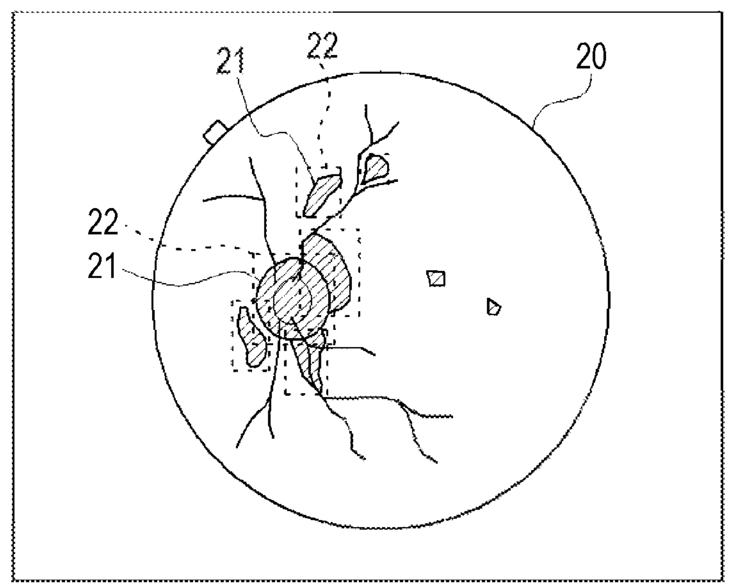
FIG. 5 is an explanatory diagram illustrating a process of extracting a high luminance region from a fundus image.
Figure 6:
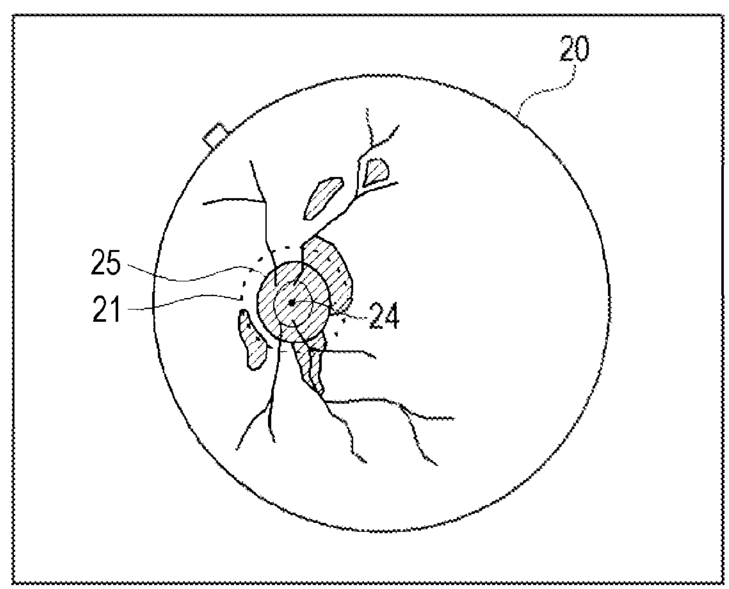
FIG. 6 is an explanatory diagram illustrating a process of detecting the number of blood vessels extending from the high luminance region.

First, in Step S21, a region of high luminance is extracted from the fundus image acquired in Step S1 (see FIG. 2). FIG. 5 illustrates an example of a fundus image 20 in which the high luminance regions 21 are extracted. In the present embodiment, the CPU 2 extracts the high luminance regions 21 by determining a threshold value such that the number of pixels extracted as the high luminance regions 21 corresponds to a predetermined proportion with respect to the number of all of the pixels in the fundus image 20. The proportion of the pixels constituting the optic disc relative to all of the pixels constituting the entire fundus image 20 falls within a certain range irrespective of the eye as the object. Thus, in the present embodiment, the threshold value for extracting the high luminance regions 21 is determined based on the proportion of the optic disc relative to the entire fundus image 20. The threshold value may be a predetermined fixed value, or a value that can be modified by the user. The threshold value may be set separately for each of the colors of RGB. The high luminance region may be extracted from a fundus image of a format other than RGB format (such as the G-value image). In Step S21, one or a plurality of regions formed by continuous (adjacent) pixels with the luminance of the threshold value or more is extracted as the high luminance regions 21. As described above, the luminance of the optic disc region is higher than the luminance of the other regions. Thus, the likelihood is high that the optic disc is included in the high luminance regions 21 extracted in Step S21.

Then, the high luminance region 21 with a small (narrow) area is eliminated from the one or the plurality of extracted high luminance regions 21 (Step S22). Specifically, in the present embodiment, the high luminance region 21 of which the number of pixels is equal to or less than a threshold value is eliminated from the object for detection for the optic disc. Generally, the optic disc region has more than a certain area. Thus, by eliminating the high luminance region 21 with a small area from the object for detection, the accuracy of detection can be increased, and the processing load on the CPU 2 can be decreased. The threshold value for extracting the high luminance regions 21 may be determined with reference to the general area of the optic disc, as needed. Alternatively, the user may be allowed to modify the threshold value.

Then, a temporary center-of-gravity position is set for each of the high luminance regions 21 (Step S23). Specifically, in the present embodiment, as illustrated in FIG. 5, a rectangular reference frame 22 surrounding each of the one or the plurality of extracted high luminance regions 21 is set, for example. The point of intersection of diagonal lines in the set reference frame 22 is set as the temporary center-of-gravity position 24 of the high luminance region 21 (see FIG. 6). The method of setting the temporary center-of-gravity position may be modified. For example, the CPU 2 calculates an average of the coordinates of a plurality of pixels constituting each of the high luminance regions 21, and sets the position of the calculated coordinates as the temporary center-of-gravity position. Alternatively, the CPU 2 may set an arbitrary position in the high luminance regions 21 as the temporary center-of-gravity position.

Then, a ring-shaped (annular) search pattern around the temporary center-of-gravity position is set (Step S24). The search pattern is a pattern for detecting the number of blood vessels extending from each of the high luminance regions 21. The optic disc has a plurality if blood vessels going in and out. In the present embodiment, therefore, the CPU 2 determines whether the number of the blood vessels extending from the high luminance region 21 is equal to or greater than a threshold value to conclude whether the high luminance region 21 includes the optic disc. The search pattern set in Step S24 is used for detecting the blood vessels. In Step S24 in the present embodiment, an annular search pattern 25 is set around the temporary center-of-gravity position 24 set in Step S23 such that it surrounds the entire high luminance region 21. The shape of the search pattern may not be a closed annular shape. The shape of the search pattern may include a rectangular ring and an open ring. The search pattern may not enclose the entirety of each of the high luminance regions 21.

Then, the CPU 2 searches the luminance values on the pattern 25. Thus, the number of blood vessels running across the search pattern 25 is detected (Step S25). In the present embodiment, the CPU 2 fits the search pattern 25 set in Step S24 on the G-value luminance difference image acquired in the G-value luminance difference image acquisition process (see FIG. 3) so as to detect the number of blood vessels on the search pattern 25. In the G-value luminance difference image, the difference between the luminance of a blood vessel and the luminance outside the blood vessel is more clearly exhibited. Therefore, the number of blood vessels can be detected with increased accuracy. Alternatively, the CPU 2 may detect the number of blood vessels by using a fundus image represented in RGB format, the G-value image, or the like. In this case, the CPU 2 detects the number of blood vessels from the luminance difference on the search pattern 25.

Of the one or the plurality of high luminance regions 21, the high luminance region 21 of which the number of the blood vessels on the search pattern 25 is equal to or greater than a threshold value (such as four) is extracted as a region including the optic disc (Step S26). As a result, the high luminance regions 21 of which the number of blood vessels extending from the high luminance regions 21 is less than the threshold value are eliminated from the optic disc candidates. Thus, the accuracy of detection of the optic disc is increased.

Figure 7:
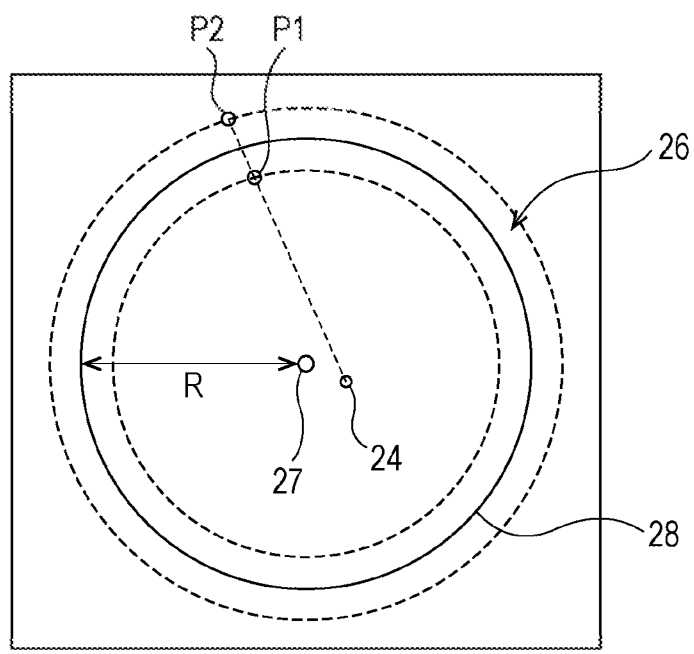
FIG. 7 is an explanatory diagram illustrating a process of detecting at contour portion and a proper center-of-gravity position of the high luminance region.

Next, a contour portion of the high luminance region 21 extracted in Step S26 is extracted. From the extracted contour portion, the proper center-of-gravity position of the high luminance region 21 is determined (Step S27). Specifically, as illustrated in FIG. 7, the CPU 2 performs an outward scan from the temporary center-of-gravity position 24 set in Step S23. In the present embodiment, the scan involves moving two measurement points P1 and P2, spaced apart from each other with a predetermined distance, outward from the temporary center-of-gravity position 24 along a scan line while the distance is maintained. In this case, a range such that the difference between the luminance at the measurement point P1 on the inside and the luminance at the measurement point P2 on the outside is equal to or greater than a threshold value is identified. The CPU 2 performs the above scan radially about the temporary center-of-gravity position 24. Thus, a ring-shaped range in which the difference in luminance between the two measurement points P1 and P2 is equal to or greater than the threshold value is extracted as a range 26 in which the contour portion of the optic disc is present. The CPU 2 then calculates an average of the pixel coordinates in the extracted range 26, and determines the calculated position as the proper center-of-gravity position 27. The specific method of extracting the contour portion of the high luminance regions 21 may be modified. For example, a certain region in which the difference in luminance between two adjacent legions (such as adjacent two pixels) is greater than a threshold value may be detected as the range 26 in which the contour portion of the optic disc is present.

Then, the CPU 2 detects the high luminance region 21 with the circular contour portion as the optic disc region by using the contour portion extracted in Step S27 and the proper center-of-gravity position 27 (Step S28). Specifically, in the present embodiment, the CPU 2 sets a circle 28 about the proper center-of-gravity position 27 while varying the radius R of the set circle 28. The CPU 2 calculates the proportion of the set circle 28 that overlaps the range 26 of the contour portion (hereafter referred to as an "overlap proportion") while varying the radius R. The CPU 2 determines the radius R at which the overlap proportion is equal to or greater than a threshold value and the highest as the radius of the optic disc. Further, the inside of the circle 28 when the overlap proportion is the highest is detected as the optic disc. On the other hand, when the circle 28 of which the overlap proportion is equal to or greater than the threshold value does not exist, this indicates that a region satisfying the substantially circular property of the optic disc is not detected. In this case, the process of Step S21 to Step S28 is repeated, or the process ends. In the present embodiment, an exactly circular optic disc is detected. However, the CPU 2 may not necessarily be configured to detect an exactly circular optic disc. For example, the CPU 2 may detect a set of points formed by connecting the intermediate points between the inner end and the outer end of the range 26 of the contour portion as the contour of the optic disc.

Next, the CPU 2 checks the luminance distribution of the detected optic disc (Step S29), and the process ends. Specifically, the CPU 2 sets two groups of concentric and circular scan lines with different radii about the proper center-of-gravity position 27. One group of scan lines is designated group A (A1 and A2), and the other group of scan lines is designated group B (B1 and B2). In this case, the radius of each scan line is set such that A1<B1<A2<B2. Further, the scan lines of the two groups are set such that the contour of the optic disc is positioned between B1 and A2. When the luminance of A1 is hider than the luminance of A2, and when the luminance of B1 is higher than the luminance of B2, the CPU 2 determines that the optic disc has been accurately detected, and ends the process. In this way, the likelihood of the high luminance region 21 which is not substantially circular being detected as the optic disc can be further decreased. The process of Step S29 may be omitted. When the optic disc detection process ends, the blood vessel detection process (see Step S6, FIG. 2) is executed.

Referring to FIGS. 8 to 11, the blood vessel detection process will be described. When the fundus image is processed to detect blood vessels, a portion in which a blood vessel being detected and another blood vessel that has been detected overlap each other ma be produced. In the present embodiment, in the blood vessel detection process, the CPU 2 can readily detect whether the branching 01 the same blood vessel, the overlapping of the roots of different blood vessels, or the intersecting of different blood vessels is present at the overlap portion.

Figure 9:
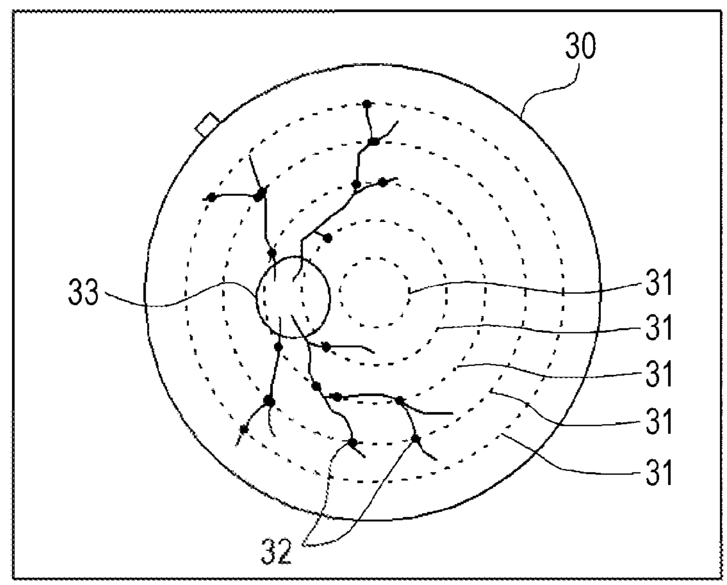
FIG. 9 is an explanatory diagram illustrating a process of detecting a seed point.

First, a seed point is detected (Step S31). The seed point refers to a base point for the detection of the central coordinates, angle, and diameter (which is the width in two-dimensional directions in the present embodiment) of a blood vessel. In the present embodiment, the CPU 2 sets a plurality of circular search lines 31 with different diameters on a G-value image 30 in a concentrically circular manner, as illustrated in FIG. 9. The CPU 2 searches the G values on the set search lines 31. The CPU 2 detects a portion in which a predetermined number or more of pixels with the G values equal to or less than a threshold value continue. The detected portion provides the seed points 32. The method of detecting the seed points 32 may be modified. For example, the CPU 2 detects the seed points by setting lattice-shaped search lines. Alternatively, the CPU 2 may detect the seed points by using a fundus image other than the G-value image (such as a fundus image of RGB format, or a G-value luminance difference image).

Next, the CPU 2 designates one of the detected seed points 32 as a seed point of interest (Step S32). The direction approaching (toward) the optic disc 33 from the seed point of interest (see FIG. 9) is the direction as a reference for investigating the direction (angle) of a blood vessel (hereafter referred to as an "investigation direction") (Step S33). The CPU 2 sets the seed point of interest as the investigation point (Step S34).

Figure 10:
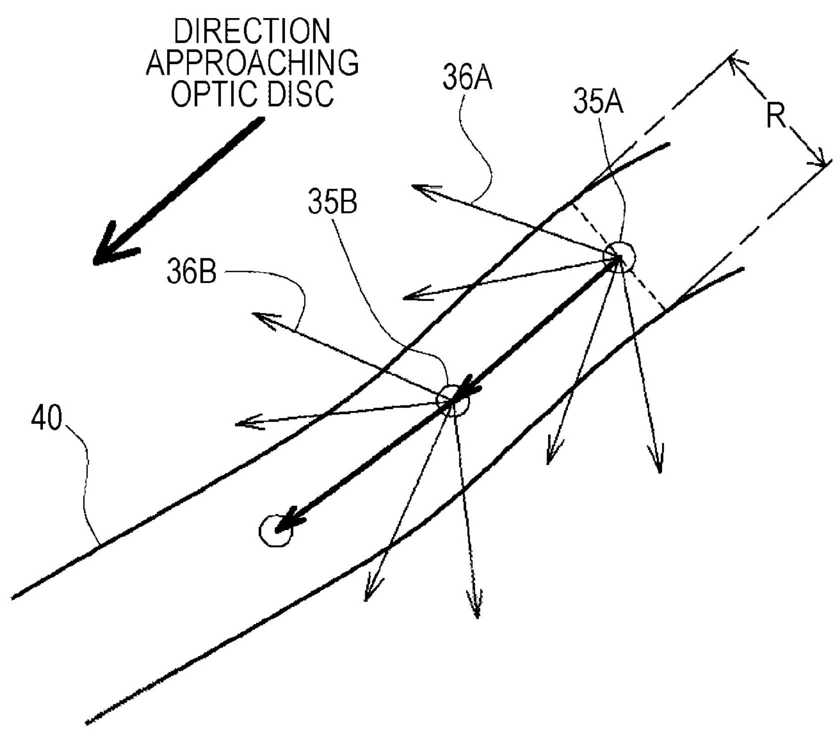
FIG. 10 is an explanatory diagram illustrating a method of investigating a blood vessel running direction and a blood vessel diameter R.

Then, the CPU 2 investigates the blood vessel running direction with reference to the set investigation point as a base point and by using the luminance value (such as the G-gradation level value in the present embodiment) (Step S36). Specifically, as illustrated in FIG. 10, the CPU 2 sets a plurality of investigation lines 36A extending radially from an investigation point 35A on the G-value image. In the present embodiment, the plurality of investigation lines 36A with a predetermined distance (such as a distance corresponding to 40 pixels in the present embodiment) is set in each of 90-degree radial ranges in the left and right directions with respect to the direction toward the optic disc. With regard to a plurality of pixels overlapping with each of the plurality of set investigation lines 36A, an average value of the G values is calculated. In the G-value image, the average value of the G values on the investigation lines 36A becomes smaller as the investigation line is closer to the center of a blood vessel 40. Thus, the CPU 2 sets the investigation line 36A with the smallest calculated average value of the G values (indicated by the thick line in FIG. 10) as a running direction specifying line. The angle (direction) of the running direction specifying line is detected as the running direction of the blood vessel 40 with respect to the investigation point 35A as the base point. The method of investigating the running direction of the blood vessel 40 may be modified. For example, the CPU 2 investigates the running direction based on the G-value luminance difference image acquired by the process of FIG. 3, instead of the G-value image. In this case, as the passing position of the investigation lines 36A are closer to the center of the blood vessel 40, the average of the luminance difference values (pixel values) on the investigation lines 36A becomes greater. By using the luminance difference image, the accuracy of detection of the running direction of the blood vessel 40 can be increased.

Then, the CPU 2 determines whether there is another blood vessel on the detected running direction specifying line that has already been detected (i.e., whether there is an overlap of a plurality of blood vessels) (Step S37). When there is no overlap portion on the running direction specifying line (Step S37: NO), the CPU 2 sets the next investigation point (Step S40). As illustrated in FIG. 10, in the present embodiment, the front end of the detected running direction specifying line is set as the next investigation point 35B, for example.

Then, the CPU 2 determines whether the next investigation point 35B that has been set is at an appropriate position (Step S41). In the present embodiment, the inside of the optic disc 33 and the outside of the image region of the fundus image are determined to be not appropriate positions. When, in the muss of Step S36, there was no investigation line 36A of which the average value of the G values was equal to or less than the threshold value, the CPU 2 also determines that the investigation is completed up to the front end portion of the blood vessel 40. In this case, the same process as when the next investigation point 35B is not at the appropriate position is performed.

When the next investigation point 35B is at the appropriate position (Step S41: YES), the CPU 2 detects the diameter of the blood vessel 40 at the current investigation point 35A (Step S42). In the present embodiment, as illustrated in FIG. 10, the width of the blood vessel 40 in a direction perpendicular to the running direction is detected as the diameter of the blood vessel 40, for example. More specifically in the present embodiment, the CPU 2 detects the width of the blood vessel 40 at a plurality of portions between the current investigation point 35A and the next investigation point 35B.

The variation of the width of the blood vessel 40 detected at the plurality of portions may fall within a predetermined range (within a range of ±2 pixels in the present embodiment). In this case, the width detected at the investigation point 35A is directly adopted as the blood vessel diameter at the investigation point 35A.

When the variation in the width of the blood vessel 40 at the plurality of portions does not fall within the predetermined range, the CPU 2 adopts an average value of the widths of the blood vessel 40 detected at the plurality of portions as the blood vessel diameter at the investigation point 35A.

In the present embodiment, the CPU 2 detects the blood vessel diameter by using the G-value luminance difference image, which clearly exhibits the difference between the luminance inside and outside blood vessels. Therefore, the accuracy of detection of the blood vessel diameter is improved. The concrete method of detecting the blood vessel diameter may also be modified. For example, the CPU 2 may not detect the width of the blood vessel 40 at a plurality of portions. The CPU 2 may detect the width of the blood vessel 40 at any portion between the current investigation point 35A and the next investigation point 35B (such as the width of the blood vessel 40 at the current investigation point 35A, or the width of the blood vessel 40 at an intermediate location between the two investigation points 35A and 35B) as the blood vessel diameter. The CPU 2 may be configured to detect the blood vessel diameter based on an image other than the G-value luminance difference image.

After the blood vessel diameter is detected, the CPU 2 registers the blood vessel central coordinates, angle, and blood vessel diameter as blood vessel data (in the HDD 5 in the present embodiment) (Step S43). The blood vessel central coordinates are the coordinates of the investigation point 35A. The angle is the angle of the blood vessel running direction investigated in Step S36. The blood vessel diameter is the value detected in Step S42. Then, the process returns to Step S36. The CPU 2 sets investigation fines 36B with reference to the next investigation point 35B as the base point, and repeats the investigation of the blood vessel running direction (see FIG. 10).

When the overlap portion (where blood vessels overlap each other) is on the detected running direction specifying line (Step S37: YES), the CPU 2 performs a branch/intersection determination process (Step S38), and the process returns to Step S36. In the branch/intersection determination process, it is detected whether the branching of the same blood vessel, the overlapping of the roots of different blood vessels, or the intersecting of different blood vessels is present a the overlap portion.

Figure 11:
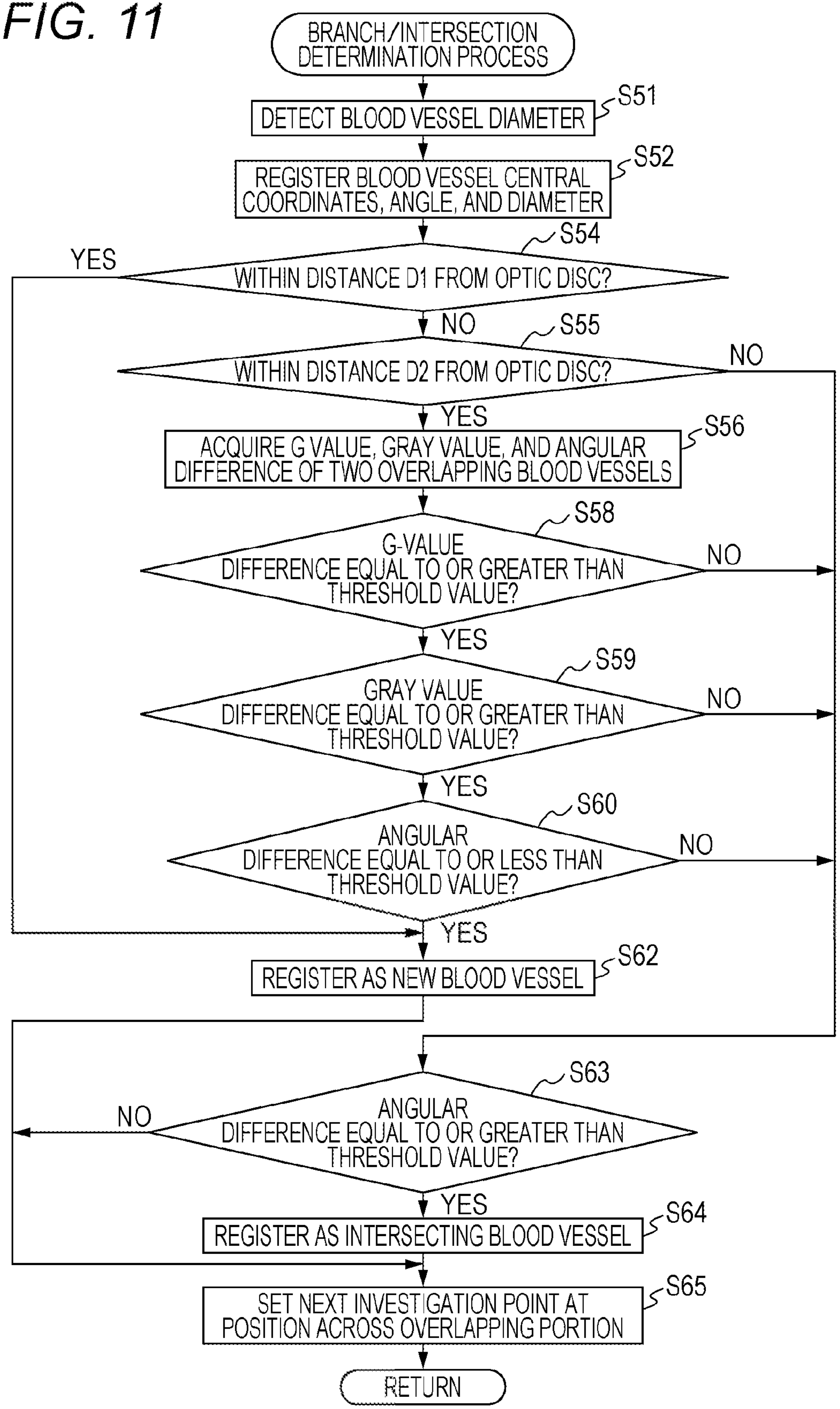
FIG. 11 is a flowchart of a branch/intersection determination process performed in the blood vessel detection process.

As illustrated in FIG. 11, at the start of the branch/intersection determination process, the blood vessel diameter is detected as in the above-described process of Step S42 and Step S43 (see FIG. 8) (Step S51). Further, the blood vessel central coordinates, angle, and blood vessel diameter are registered (Step S52). Then, it is determined whether the overlap portion is within the range of a distance D1 (such as 1.2 times the radius of the optic disc in the present embodiment) from the center of the optic disc 33 (Step S54). Most of the blood vessels in the fundus extend radially from the optic disc and the vicinity thereof. Thus, when the overlap portion is within the range of the distance D1 from the optic disc center (Step S54: YES), the blood vessel under investigation is registered as a new blood vessel different from other blood vessels (Step S62), and the process proceeds to Step S65. Namely, in Step S62, the fact that the blood vessel under investigation and a blood vessel that has been detected are overlapping each other at the root portions of the blood vessels is stored in the HDD 5.

When the overlap portion is not within the range of the distance D1 from the optic disc center (Step S54: NO), the CPU 2 determines whether the overlap portion is within the range of a distance D2 (>D1) from the optic disc center. In the present embodiment, D2 is 1.4 times the radius of the optic disc, for example. The value of the distance D1 and the value of the distance D2 may be modified.

Outside the range of the distance D2, the likelihood of the presence of a new blood vessel (i.e., the presence of the root portion of a blood vessel) is low. Thus, when the overlap portion is not within the range of the distance D2 from the optic disc center (Step S55: NO), it is determined whether the branching of the same blood vessel, or the intersecting of different blood vessels is present at the overlap portion (Step S63). Specifically, in the present embodiment, it is determined whether the angular difference between two blood vessels at the overlap portion is equal to or greater than a threshold Value (Step S63). When the same blood vessel is branched, the angular difference of two branch blood vessels falls within a substantially constant range. Thus, when the angular difference is less than the threshold value (such as 40 degrees in the present embodiment) (Step S63: NO), the CPU 2 registers the fact that the branching of the same blood vessel is present at the overlap portion, and causes the process to proceed to Step S65. Namely, when the angular difference is less than the threshold value, the overlap portion of the two blood vessels is considered to be a branching portion at which the same blood vessel is branched. When the angular difference is equal to or greater than the threshold value (Step S63: YES), the fact that different blood vessels are intersecting each other is registered (Step S64), and the process proceeds to Step S65. Namely, when the angular difference is equal to or greater than the threshold value, the overlap portion of the two blood vessels is considered to be an intersecting portion at which different blood vessels intersect each other.

Within the range outside the distance D1 and inside the distance D2, a new blood vessel may be present, and also branching or intersection may be present. Thus, in the present embodiment, when the overlap portion is not within the range of the distance D1 but within the range of the distance D2 (Step S55: YES), the CPU 2 determines whether a new blood vessel is present based on the luminance, gray value, and angular difference of the blood vessel (Step S56 to Step S60). Namely, when the difference in the luminance and/or the gray value difference of two overlapping blood vessels are large, and the angular difference is small, it is determined that there is a new blood vessel.

Specifically, the CPU 2 first acquires the G value and gray value of each of the overlapping blood vessels, and the angular difference between the two blood vessels (Step S56). For example, the G value acquired in Step S56 includes the standard deviation of the value at the overlap portion of each of the blood vessels. An example of the gray value acquired in Step S56 is the average value of gray values at the overlap portion of each of the blood vessels. In Step S56, any value for comparing the two overlapping blood vessels may be acquired. Therefore, a value different from the above values may be acquired. Then, the CPU 2 determines whether the difference in the acquired G values (the standard deviations of the G values in the present embodiment) is equal to or greater than a threshold value (Step S58). When the difference in G values is less than the threshold value (Step S58: NO), the process proceeds to the determination in Step S63. When the difference in G values is equal to or greater than the threshold value (Step S58: YES), it is determined whether the difference in gray values is equal to or greater than a threshold value (Step S59). When the difference in gray values is less than the threshold value (Step S59: NO), the process proceeds to the determination in Step S63. When the difference in gray values is equal to or greater than the threshold value (Step S59: YES), it is determined whether the angular difference between the two blood vessels is equal to or less than a threshold value (Step S60). When the angular difference between the two blood vessels is greater than the threshold value (Step S60: NO), the process proceeds to the determination in Step S63. When the angular difference between the two blood vessels is equal to or less than the threshold value (Step S60: YES), the blood vessel under investigation is registered as a new blood vessel (Step S62), and the process proceeds to Step S65.

Then, the CPU 2 sets the next investigation point at a position across the overlap portion of the two blood vessels (Step S65), and the process returns to the blood vessel detection process. When there is the branching of the same blood vessel at the overlap portion, no blood vessel exists at the position across the overlap portion. In this case, at the end of the branch/intersection determination process (Step S38) in the blood vessel detection process (see FIG. 8), the CPU 2 may cause the process to transition to the determination in Step S45 instead of returning the process to Step S36.

Referring back to the description of FIG. 8, when the next investigation point is not at the appropriate position (Step S41: NO), the CPU 2 determines whether the investigation in the two directions (i.e., the direction toward the optic disc and the direction away from the optic disc) has been completed (Step S45). When the investigation is completed in only one direction (Step S45: NO), the investigation direction is reversed to the direction away from the optic disc (Step S46), and the process returns to Step S36. As a result, the entire blood vessel from the root to front end is detected with reference to the seed point 32 as the base point. When the investigation in the two directions is completed (Step S45: YES), the CPU 2 determines whether the process is completed for all of the seed points 32 (Step S47). When the process for all of the seed points 32 is not completed (Step S47: NO), the CPU 2 modifies the seed point of interest to the seed point 32 that is yet to be processed (Step S48), and the process returns to Step S33.

When the process is completed for all of the seed points 32 (Step S47: YES), a process of forming a blood vessel tree is executed (Step S49). Specifically, first, the CPU 2 registers a blood vessel located within a predetermined distance (which is 1.6 times the optic disc radius in the present embodiment) from the optic disc center as a base point blood vessel. A blood vessel that is not located in the predetermined distance from the optic disc center is registered as a floating blood vessel. Then, the CPU 2 determines whether the base point blood vessel exists within the range of a predetermined distance (such as a distance corresponding to 50 pixels in the present embodiment) and a predetermined angle (such as 60 degrees with respect to the front end direction or the rear end direction in the present embodiment) from the ends (front end and rear end) of the floating blood vessel. When the base point blood vessel exists in at least one of the investigation range from the front end and the investigation range from the rear end, the CPU 2 registers the floating blood vessel being investigated as a part of the base point blood vessel within the investigation range. From the above process, a plurality of regions of the blood vessel that has been detected in divided state can be joined. Thereafter, the CPU 2 ends the blood vessel detection process, and executes the arteriovenous diameter ratio calculation process (see Step S7 in FIG. 2).

Referring to FIGS. 12 to 16, the arteriovenous diameter ratio calculation process will be described. In the arteriovenous diameter ratio calculation process of the present embodiment, the CPU 2 calculates the arteriovenous diameter ratio in each of a region above the height of the optic disc (hereafter referred to as an "upper region") and a region under the height of the optic disc (hereafter referred to as a "lower region"). As a result, compared with conventional technology, the accuracy of calculation of the arteriovenous diameter ratio is improved.

Figure 12:
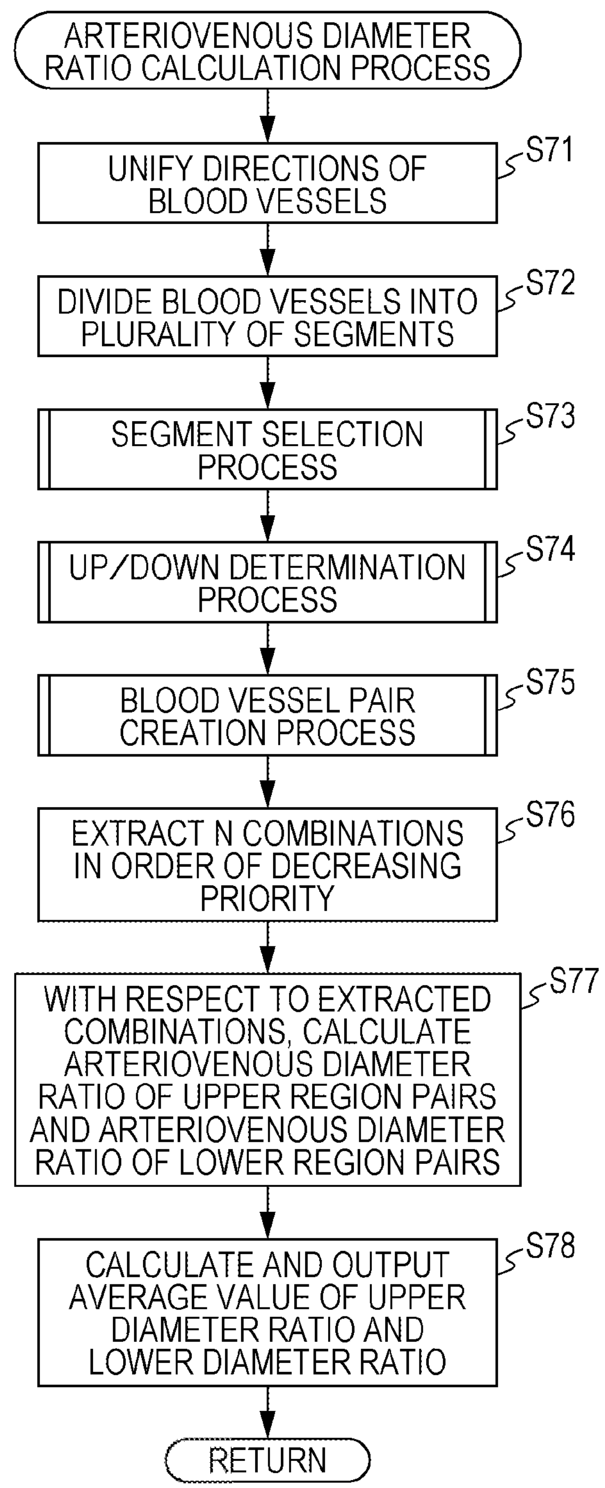
FIG. 12 is a flowchart of an arteriovenous diameter ratio calculation process performed in the fundus image process.

As illustrated in FIG. 12, at the start of the arteriovenous diameter ratio calculation process, the CPU 2 unifies the directions of the plurality of blood vessels detected (identified) in the blood vessel detection process (see FIG. 8) with reference to the optic disc (Step S71). In the present embodiment, the coordinates of the ends of the blood vessels indicated by the blood vessel data are acquired. Of the ends of the blood vessels, the end closer to the optic disc and the end farther from the optic disc are identified by the acquired coordinates. The CPU 2 unifies the directions of the blood vessels in each of the blood vessel data such that the end closer to the optic disc is at the root while the end farther from the optic disc is at the front end.

Figure 13:
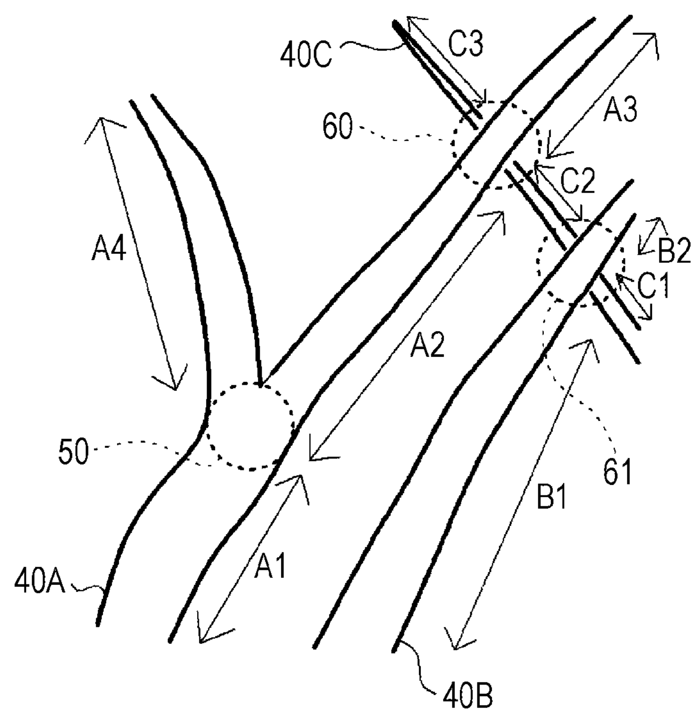
FIG. 13 is an explanatory diagram illustrating a process of dividing the blood vessels into a plurality of segments.

Then, the CPU 2 divides each of the identified blood vessels into a plurality of segments. The dividing is perforated with respect to at least a branching portion and an intersecting portion of the blood vessels as end points (Step S72). In an example shown in FIG. 13, three blood vessels 40A, 40B, and 40C are illustrated. The blood vessel 40A includes a branching portion 50. The blood vessel 40C intersects the blood vessel 40A, forming an intersecting portion 60, while intersecting the blood vessel 40B, forming an intersecting portion 61. In the present embodiment, in the blood vessel detection process performed in the branch/intersection determination process (see FIG. 11), the branching portion 50 and the intersecting portion 60 are detected in addition to the blood vessel data. The CPU 2 divides each of the blood vessels 40A, 40B, and 40C at the branching portion 50 and the intersecting portion 60 as the end points, thus forming the segments. As a result, in the example shown in FIG. 13, the blood vessel 40A is divided into four segments A1, A2, A3, and A4 at the branching portion 50 and the intersecting portion 60 as the end points. The blood vessel 40B is divided into two segments B1 and B2 at the intersecting portion 61 as the end point. The blood vessel 40C is divided into three segments C1, C2, and C3 at the two intersecting portions 60 and 61 as the end points. In the example of FIG. 13, the blood vessels 40A to 40C are divided at only the branching portion and the intersecting portions as the end points. However, the CPU 2 may allocate an end point other than the branching portion and the intersecting portion. For example, the CPU 2 allocates an end point at a portion of the blood vessel at which there is neither the branching portion nor the intersecting portion in order to make the length of each of the segments as uniform as possible, and then divides the blood vessel at the end point. In this case, the accuracy of calculation of the arteriovenous diameter ratio may be further improved. The accuracy of calculation can be more improved by dividing the blood vessel into segments. However, the CPU 2 may be configured to calculate the arteriovenous diameter ratio without dividing the blood vessel into segments.

Thereafter, a segment selection process is executed (Step S73). In the segment selection process, the CPU 2 selects from the plurality of segments divided in Step S72 segments which are appropriate as the object for calculating the arteriovenous diameter ratio. By eliminating segments of which the likelihood of being inappropriate as the object for calculation is high, the processing load on the CPU 2 is decreased while the accuracy of calculation is improved.

Figure 14:
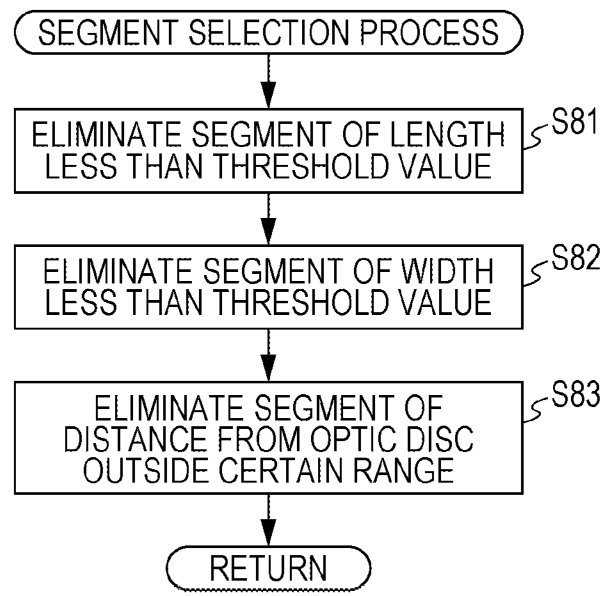
FIG. 14 is a flowchart of a segment selection process performed in the arteriovenous diameter ratio calculation process.

As illustrated in FIG. 14, in the segment selection process, the CPU 2 eliminates a segment whose length in the blood vessel running direction is less than a threshold value (second threshold value) from the segments as the object for calculating the arteriovenous diameter ratio (Step S81). Too short a segment tends to readily reflect the influence of an error, such as noise. In the present embodiment, the CPU 2 selects the segments with lengths equal to or greater than the threshold value (second threshold value) as the object for calculation of the arteriovenous diameter ratio. Thus, the influence of noise and the like can be decreased.

Then, the CPU 2 eliminates a segment whose width (diameter) in a direction intersecting (or orthogonal to, in the present embodiment) the blood vessel running direction is less than a threshold value (third threshold value) from the segments as the object for calculation (Step S82). A segment with too small a width has a high likelihood of being positioned at the end of a blood vessel. In the present embodiment, the CPU 2 selects the segments whose widths are equal to or greater than the threshold value (third threshold value) as the object for calculation of the arteriovenous diameter ratio. Thus, the likelihood of the arteriovenous diameter ratio being calculated based on the end of a blood vessel can be decreased. Accordingly, a decrease in accuracy of calculation can be suppressed.

The CPU 2 then eliminates a segment whose distance from the optic disc is outside a certain range from the segments as the object for calculation (Step S83). In a region with too short a distance from the optic disc, the root portions of a plurality of blood vessels may be overlapping and entangled with each other. In this case, arteries and veins do not easily run side by side. On the other hand, in a region with too great a distance from the optic disc, there tends to be a number of segments thinned by being repeatedly bent or branched. Therefore, such segments (regions) are not suitable as the object for comparing the diameter of an artery and the diameter of a vein. In the present embodiment, segments in a region whose distance from the optic disc is equal to or less than a threshold value Q1 (such as a region whose distance from the optic disc center is equal to or less than 1.5 times the optic disc radius), and segments in as region whose distance from the optic disc is equal to or greater than a threshold value Q2 (>Q1) are eliminated from the segments as the object for calculation. The threshold values Q1 and Q2 for determining the region as the object for calculation may be set as needed. Preferably, both the region with too short a distance from the optic disc, and the region with too great a distance from the optic disc may be eliminated from the segments as the object for calculation. However, the segments of only one of the regions may be eliminated. The threshold values used in Step S81 to Step S83 may be set as needed, or may be modified by the user.

The CPU 2 may be configured to determine a blood vessel pair as the object for calculation from segments whose distance from the optic disc is equal to or less than Q2 (fourth threshold value). Q1 may be the distance from the optic disc to the measurement point P1 (see FIG. 7). Moreover, Q2 may be the distance from the optic disc to the measurement point P2 (see FIG. 7).

Referring back to the description of FIG. 12, when the segment selection process is completed (Step S73), the CPU 2 performs an up/down determination process (Step S74). In the up/down determination process, it is determined whether the segments are positioned in the upper region above the height of the optic disc (or the height of the center of the optic disc in the present embodiment), or positioned in the lower region under the height of the optic disc. It is also determined whether the segments are artery segments, vein segments, or segments that are not clearly decided to be an either artery or a vein (hereafter referred to as “unclear segments”).

As illustrated in FIG. 15, at the start of the up/down determination process, the CPU 2 selects one of the plurality of segments selected in the segment selection process (see FIG. 14) as an object segment (Step S91). Then, the CPU 2 acquires information indicating the height at the center of the object segment (Step S92). For example, in the present embodiment, an average value of the Y-coordinate at the front end and the Y-coordinate at the rear end of the object segment are acquired as the information indicating the height at the center of the object segment.

Then, the CPU 2 determines whether the region in which the object segment is positioned is an upper region higher than (i.e., above) the optic disc (Step S94). In the present embodiment, the Y-coordinate indicating the height at the center of the object segment, and the Y-coordinate at the center of the optic disc are compared. Thus, it is determined whether the region of the object segment is an upper region.

When the position of the object segment is higher than the optic disc; i.e., when the object segment is positioned in the upper region (Step S94: YES), the CPU 2 determines whether the object segment is an artery (Step S95). Generally, in the fundus, an artery is brighter and thinner than a vein (Namely, veins are darker and thicker than arteries). The CPU 2 determines whether, by using at least one of the luminance of the pixels constituting the segment and the diameter of the segment (width of the segment), the segment or the blood vessel constituted by a plurality of segments is an artery or a vein. The determination of whether the blood vessel is an artery or a vein may be executed in the above-described blood vessel detection process (see FIG. 8). When the object segment is an artery (Step S95 YES), the object segment is registered as an artery segment of the upper region (Step S96), and the process proceeds to the determination in S107. When the object segment is not an artery (Step S95: NO), it is determined whether the object segment is a vein (Step S97). When the object segment is a vein (Step S97: YES), the object segment is registered as a vein segment of the upper region (Step S98), and the process proceeds to the determination in Step S107. When the determination of whether the blood vessel is an artery or a vein with respect to the object segment cannot be made (Step S97: NO), the object segment is registered as an unclear segment of the upper region (Step S99), and the process proceeds to the determination in Step S107.

When the position of the object segment is lower than the optic disc; i.e., when the object segment is positioned in the lower region (Step S94: NO), the CPU 2 also makes the determination of whether the blood vessel is an artery or a vein as in when positioned in the upper region. When the object segment is an artery (Step S101: YES), the object segment is registered as the artery segment of the lower region (Step S102). When the object segment is not an artery (Step S101: NO) but a vein (Step S103: YES), the object segment is registered as a vein segment of the s lower region (Step S104). When the object segment is neither an artery nor a vein (Step S103: NO), the object segment is registered as an unclear segment of the lower region (Step S105), and the process proceeds to the determination in Step S107.

Then, the CPU 2 determines whether the process is completed for all of the segments (Step S107). When there are segments that are yet to be designated as an object segment (Step S107: NO), the process returns to Step S91, and the determination process for the segments is performed (Step S91 to S105). When all of the segments have been designated as the object segment (Step S107: YES), the process returns to the arteriovenous diameter ratio calculation process (see FIG. 12). Then, a blood vessel pair creation process is executed (Step S75). In the blood vessel pair creation process, a pair of an artery segment and a vein segment as the object for calculation of the arteriovenous diameter ratio (hereafter referred to as a "blood vessel pair") is created.

Figure 16:
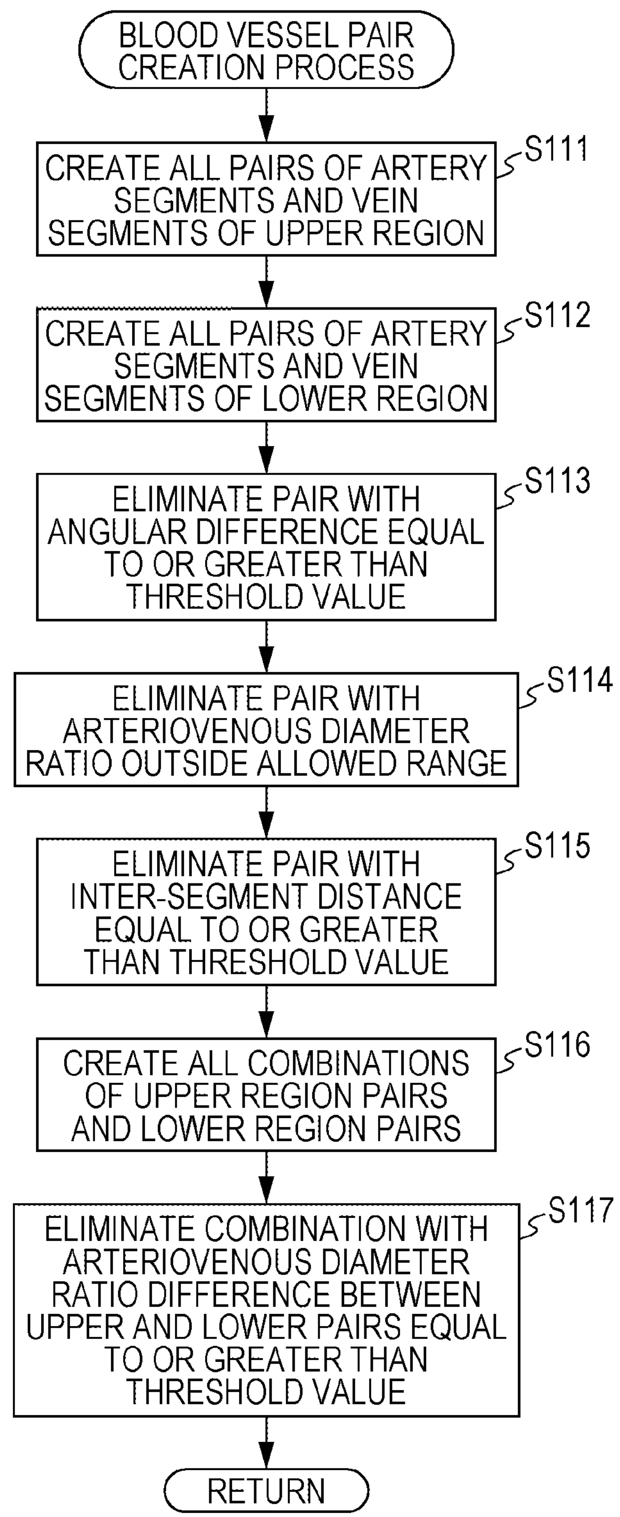
FIG. 16 is a flow chart of a blood vessel pair creation process performed in the arteriovenous diameter ratio calculation process.

As illustrated in FIG. 16, at the start of the blood vessel pair creation process, the CPU 2 first creates blood vessel pairs from all of pairs of each of one or a plurality of artery segments in the upper region, and each of one or a plurality of vein segments in the upper region (Step S111). Further, the CPU 2 creates blood vessel pans from all of pairs of each of one or a plurality of artery segments in the lower region and each of one or a plurality of vein segments in the lower region (Step S112). Namely, in each or the upper region and the lower region, the blood vessel pairs are created separately. In the present embodiment, the CPU 2 creates the blood vessel pairs from all of the artery segments and the vein segments selected in the same region. Therefore, a single segment could be a segment constituting a plurality of pairs. Thus, compared with when only a blood vessel pair serving as the object for calculation of the arteriovenous diameter ratio is created, the likelihood of creation of a blood vessel pair suitable as the object for calculation is increased.

Then, from among the plurality of blood vessel pairs that have been created, a blood vessel pair of which the angular difference between the artery segment and the vein segment is equal to or greater than a threshold value (fifth threshold value) is eliminated from the object for calculation (Step S113). In order to improve the accuracy of calculation of the arteriovenous diameter ratio, it is preferable to calculate the diameter ratio from an artery and a vein that run side by side at an angle as close to being parallel to each other as possible. In the present embodiment, the CPU 2, when identifying a blood vessel in the blood vessel detection process (see FIG. 8), acquires the information about the central coordinates, angle, and diameter of the blood vessel. The CPU 2 calculates the angular difference between the two segments constituting the blood vessel pair. The CPU 2 eliminates a blood vessel pair with an angular difference equal to or greater than the threshold value (fifth threshold value) from the object for calculation. In the present embodiment, the CPU 2 takes into account the case in which a segment is curved. Namely, the CPU 2 calculates an average value of a plurality of pieces of angle information corresponding to a single segment. Using the average value, the CPU 2 acquires a difference between the angle of the artery segment and the angle of the vein segment. Thus, the accuracy of calculation of the angular difference is improved. However, the CPU 2 may execute the process of Step S113 by using at least one of a plurality of pieces of angle information corresponding to a single segment. The angular difference threshold value (fifth threshold value) may be set as needed. The user may be allowed to modify the threshold value. Further, the CPU 2 may calculate an upper diameter ratio or the lower diameter ratio by using a blood vessel pair of which the angular difference between the two segments is equal to or less than the fifth threshold value.

The CPU 2 then calculates the arteriovenous diameter ratio with respect to all of the created blood vessel pairs. Further, the CPU 2 eliminates a blood vessel pair of which the arteriovenous diameter ratio is outside an allowable range from the object for calculation (Step S114). The accurately calculated arteriovenous diameter ratio falls within a certain range even when the influence of hypertension and the like is taken into consideration. Therefore, the CPU 2 eliminates the blood vessel pair of which the arteriovenous diameter ratio is outside the allowable range from the object for calculation. Namely, the CPU 2 calculates the arteriovenous diameter ratio by using pairs of which the result of calculation of the upper diameter ratio and the lower diameter ratio falls within the allowable range. In this way, the likelihood of calculating the arteriovenous diameter ratio based on an inappropriate blood vessel pair can be decreased. For example, in the present embodiment, when the arteriovenous diameter ratio is calculated by dividing the diameter of an artery by the diameter of a vein, a blood vessel pair of which the arteriovenous diameter ratio is equal to or greater than 1.0 is eliminated as an inappropriate blood vessel pair. The CPU 2 may execute the process of Step S114 based on an allowable range of the arteriovenous diameter ratio set by the user.

Then, the CPU 2 eliminates a blood vessel pair of which the interval (segment interval) between the artery segment and the vein segment constituting the blood vessel pair is equal to or greater than a threshold value from the object for calculation (Step S115). When the interval (segment interval) between the artery and the vein is long, the likelihood of the two blood vessels running side by side is low. Thus, it would be inappropriate to use such a pair as the object for calculation of the arteriovenous diameter ratio. In the present embodiment, the CPU 2 eliminates the blood vessel pair of which the segment interval is equal to or greater than the threshold value. In this way, the accuracy of calculation of the arteriovenous diameter ratio can be improved. The threshold value that is referenced may be set as needed. In the present embodiment, the direction of the segments is sorted with reference to the position of the optic disc. Thus, the CPU 2 can distinguish the front end side from the rear end side of the segments. Accordingly, the CPU 2 calculates an average value of the interval between the coordinates at the front end and the interval between the coordinates at the rear end (root side) of the two segments as the interval of the two segments. However, the CPU 2 may calculate the interval of the two segments by a different method. For example, the CPU 2 identifies the center of each of the segments, and then calculates the distance between the centers as the segment interval. The CPU 2 may calculate the minimum distance between the two segments as the segment interval.

Thereafter, the CPU 2 creates all combinations of each of one or a plurality of blood vessel pairs (hereafter referred to as the "upper region pairs") created in the upper region, and each of one or a plurality of blood vessel pairs (hereafter referred to as the "lower region pairs") created in the lower region (Step S116). The CPU 2 eliminates from the object for calculation a combination of the created plurality of combinations in which the difference between the arteriovenous diameter ratio in the upper region pairs (upper diameter ratio) and the arteriovenous diameter ratio in the lower region pairs (lower diameter ratio) is equal to or greater than a threshold value (Step S117). A difference is normally not caused between the diameter ratio of an artery and a vein running upward and side by side arid the diameter ratio of an artery and a vein running downward and side by side. Thus, the calculation accuracy can be confirmed depending on whether the difference between the arteriovenous diameter ratio in the upper region pairs and the arteriovenous diameter ratio in the lower region pairs is equal to or greater than a threshold value (first threshold value). By eliminating the combination of which the arteriovenous diameter ratio difference is equal to or greater than the threshold value (first threshold value), the CPU 2 increases the accuracy of calculation. The blood vessel pair creation process is thus completed, and the process returns to the arteriovenous diameter ratio calculation process.

Referring back to the description of FIG. 12, when the blood vessel pair creation process is completed (Step S75) the CPU 2 extracts, from the combinations of the upper region pairs and the lower region pairs that were not eliminated in Step S117 (see FIG. 16), N combinations in the order of decreasing priority (Step S76). In the present embodiment, the arteriovenous diameter ratio is calculated preferentially for blood vessel pairs with shorter segment interval (i.e., by giving the blood vessel pairs with shorter segment interval higher priority). As a result, the arteriovenous diameter ratio is more accurately calculated based on the diameter of segments close to each other (with the higher likelihood of running side by side).

In the present embodiment, in Step S76, the CPU 2 extracts a single combination with the smallest sum of the segment interval in the upper region pair and the segment interval in the lower region pair. However, the CPU 2 may extract a plurality of combinations in the order of decreasing priority. In the present embodiment, in Step S116, all combinations of each of the upper region pairs and each of the lower region pairs are created. Thus, a single blood vessel pair could be a constituent element of a plurality of combinations. When extracting a plurality of combinations in Step S76, the CPU 2 may extract a plurality of combinations including the same blood vessel pair as a constituent element, or the overlapping of the same blood vessel pair may be prohibited.

The CPU 2 may not execute the process of creating the combinations of the upper region pairs and the lower region pairs (see Step S116, Step S117, and FIG. 16) In this case, in Step S76, the CPU 2, instead of extracting the N combinations of the upper region pairs and the lower region pairs, may extract N upper region pairs and N lower region pairs separately in the order of increasing segment interval.

The order of priority for extracting the blood vessel pairs or the combinations of the blood vessel pairs may be modified. For example, the CPU 2 preferentially extracts blood vessel pairs with smaller angular difference between the segments, as well as considering the segment interval. Alternatively, the CPU 2 may preferentially extract blood vessel pairs with smaller distance from the optic disc. When the blood vessel pairs or the combinations of blood vessel pairs are extracted by using a plurality of parameters, the CPU 2 may perform weighting of each parameter.

Then, with respect to the extracted blood vessel pairs (which are combinations of blood vessel pairs in the present embodiment), the CPU 2 calculates the diameter ratio of the artery and vein constituting the extracted upper region pairs (hereafter referred to as the "upper diameter ratio"), and the diameter ratio of the artery and vein constituting the lower region pairs (hereafter referred to as the "lower diameter ratio") (Step S77). For example, in the present embodiment, when information about a plurality of diameters is associated with a single segment, the arteriovenous diameter ratio is calculated based on an average value of the corresponding plurality of diameters. However, the arteriovenous diameter ratio may be calculated based on some of the information about the corresponding diameter (such as the information about diameter at the center of the segment). When a plurality of upper region pairs is extracted in the process of Step S76, the CPU 2 may calculate the diameter ratio with respect to each of the plurality of extracted upper region pairs. In this case, the CPU 2 may use an average value of calculation results as the upper diameter ratio. The same applies to a case in which a plurality of lower region pairs is extracted.

The CPU 2 then calculates an average value of the calculated upper diameter ratio and the lower diameter ratio as a representative value of the arteriovenous diameter ratio of the examinee's eye. The CPU 2 outputs the calculated arteriovenous diameter ratio to at least one of the HDD 5, the monitor 13, the external device, and the like (Step S78), and the process ends. In the present embodiment, in Step S78, in addition to the average value of the upper diameter ratio and the lower diameter ratio, the upper diameter ratio and the lower diameter ratio are also output. Thus, the examiner (user) can conduct a useful diagnosis by considering the upper diameter ratio and the lower diameter ratio separately.

As described above, in the present embodiment, the PC 1 calculates the diameter ratio of the blood vessels positioned in the upper region above the height of the optic disc, and also the diameter ratio of the blood vessels positioned in the region under the height of the optic disc. The blood vessels in the fundus tend to include arteries and veins running side by side over and under the optic disc. Thus, when the arteriovenous diameter ratio is calculated by using the upper region blood vessels and the lower region blood vessels as a group, the likelihood of the arteriovenous diameter ratio being calculated from arteries and veins that are not running side by side is increased, whereby a useful result may not be obtained. One of the typical effects obtained by the present embodiment is that the arteriovenous diameter ratio can be calculated from the arteries and veins running side by side in each of the upper region and the lower region, whereby the arteriovenous diameter ratio can be calculated more accurately than the conventional art. Another effect is that the examiner can gain a calculation result in which the arteriovenous diameter ratio of the upper region and the arteriovenous diameter ratio of the lower region are both considered. In this way, the examiner can perform an effective diagnosis.

In the present embodiment, the PC 1 (CPU 2) divides identified blood vessels into a plurality of segments on data while using at least a branching portion and an intersecting portion of the blood vessels as end points. The PC 1 creates a pair of two segments (blood vessel pair) from the plurality of divided segments, and calculates the diameter ratio of the segments in the created blood vessel pair. In this case, the PC 1 can calculate the arteriovenous diameter ratio without being affected by the influence of the branching portion and the intersecting portion.

In the present embodiment, when a plurality of groups of blood vessel pairs is determined, the PC 1 preferentially calculates the arteriovenous diameter ratio of a blood vessel pair with shorter segment interval. In this case, the PC 1 can calculate the arteriovenous diameter ratio with increased accuracy based on the diameter of blood vessels with smaller mutual distance (i.e., with the greater likelihood of the blood vessels running side by side).

A difference is not normally caused between the diameter ratio of an artery and a vein running upward and side by side (upper diameter ratio) and the diameter ratio of an artery and a vein running downwardly side by side (lower diameter ratio). Thus, when the difference between the upper diameter ratio and the lower diameter ratio is large, there is the possibility of a calculation error. In the present embodiment, the PC 1 eliminates the combination of blood vessel pairs of which the difference between the upper diameter ratio and the lower diameter ratio is equal to or greater than a threshold value (first threshold value) from the object for calculation of the arteriovenous diameter ratio. In this way, the accuracy of calculation can be further increased.

A segment that is too short tends to reflect the influence of error such as noise. In the present embodiment, the PC 1 creates the blood vessel pair from segments of lengths equal to or greater than a threshold value (second threshold value). In this way, the influence of noise and the like can be decreased.

A segment with too small a width the diameter is too small) have a high likelihood of being positioned at the end of a blood vessel. Generally, the blood vessels in the fundus become thinner toward the end. Therefore, it is difficult to obtain an arteriovenous diameter ratio effective for diagnosis at the end of a blood vessel. In the present embodiment, the PC 1 creates the blood vessel pair from segments of which the width is equal to or greater than a threshold value (third threshold value). In this way, the calculating of the arteriovenous diameter ratio from the end of the blood vessel can be avoided. Thus, a decrease in calculation accuracy is limited.

In most cases, the blood vessels in the fundus extend away from the optic disc. Thus, a segment too far from the optic disc has a high likelihood of being positioned at the end of a blood vessel. In the present embodiment, the PC 1 creates the blood vessel pair from segments of which the distance from the optic disc is equal to or less than a threshold value (fourth threshold value). In this way, the calculating of the arteriovenous diameter ratio from the end of a blood vessel can be avoided. Thus, a decrease in calculation accuracy can be limited.

By calculating the arteriovenous diameter ratio from an artery and a vein running side by side at an angle as close to being parallel as possible, the accuracy of calculation is improved. In the present embodiment, the PC 1 calculates the arteriovenous diameter ratio from the blood vessel pair of which the angular difference of two segments is equal to or less than a threshold value (fifth threshold value). In this way, the accuracy of calculation can be further increased.

The accurately calculated arteriovenous diameter ratio falls within a certain range even when taking the influence of hypertension and the like into consideration. In the present embodiment, the PC 1 use the blood vessel pairs if which the result of calculation of the upper diameter ratio or the lower diameter ratio falls within an allowable range as the object for calculation. Thus, the likelihood of the arteriovenous diameter ratio being calculated from an inappropriate blood vessel pair can be decreased.

Further, in the present embodiment, the PC 1 is provided with a configuration for detecting the optic disc and a configuration for detecting a blood vessel, in addition to the configuration for calculating the arteriovenous diameter ratio. For example, in the present embodiment, the PC 1 includes as fundus image processing apparatus that detects the optic disc from a fundus image of the examinee's eye by processing the fundus image. The PC 1 is provided with: a region extraction unit that extracts from the fundus image one or a plurality of high luminance regions in which a set of pixels with luminance values equal to or greater than a predetermined threshold value is formed; a blood vessel number detection unit that detects from the fundus image the number of blood vessels running across the inside and outside of the high luminance region extracted by the region extraction unit; and an optic disc detection unit that detects, as an optic disc region, a high luminance region of which the number of blood vessels detected by the blood vessel number detection unit is equal to or greater than a predetermined threshold value. A plurality of blood vessels runs into and out of the optic disc. Thus, the PC 1 can distinguish the optic disc from vitiligo and flare and the like depending on whether the number of blood vessels running across the inside and outside of the region is equal to or greater than the threshold value, and accurately detect the optic disc.

In the present embodiment, the PC 1 searches luminance values on a ring-shaped search pattern set at the position at which the high luminance region has been extracted. By detecting the number of the blood vessels running across the search pattern, the number of blood vessels running across the inside and outside of the high luminance region is detected. In this case, the PC 1 can detect the number of the blood vessels running across the inside and outside of the high luminance region by simply searching the luminance values on the ring-shaped search pattern even when the blood vessels are not accurately detected.

In the present embodiment, the PC 1 detects the number of blood vessels by using at least one of the G value and the B value of the fundus image represented in RGB format. The colors of green and blue are more readily absorbed by a blood vessel than the color of red. Thus, the influence of the presence or absence of the blood vessel is more readily exhibited in the G value and B value of the fundus image than in the R value. Thus, by using at least one of the G value and the R value, the PC 1 can increase the accuracy of detection of the number of blood vessels.

In the present embodiment, the PC 1 is further provided with an elimination unit that determines whether the high luminance region extracted by the region extraction unit is substantially circular, and that eliminates the high luminance region determined to be not substantially circular from a candidate for the optic disc region. Generally, the optic disc is substantially circular. The PC 1 eliminates the high luminance region that is not substantially circular from the optic disc region. In this way, the accuracy of detection of the optic disc can be further increased.

In the present embodiment, the PC 1 sets a circular scan line at the contour portion of the high luminance region, and determines the proportion of pixels of which the luminance value equal to or greater than as threshold value to pixels positioned on the set scan line. In this way, it is determined whether the high luminance region is substantially circular. Thus, the PC 1 accurately determine whether the high luminance region is substantially circular.

Further, in the present embodiment, the PC 1 includes a fundus image processing apparatus that detects a blood vessel from the fundus image by processing the fundus image of the examinee's eye. The PC 1 is provided with: a position/direct on detection unit that detects the position and running direction of the blood vessel on the fundus based on a luminance value in the fundus image; an overlap position detection unit that detects an overlap position of a plurality of blood vessels of which the position and running direction has been detected by the position/direction detection unit; and a determination unit that determines whether the branching of the same blood vessel, the overlapping of the roots of different blood vessels, or the intersecting of different blood vessels is present at the overlap position. Thus, in the present embodiment, the PC 1 can more accurately detect the blood vessel.

The present disclosure is not limited to the above embodiment. It is obvious that the present disclosure may be variously modified. For example, the PC 1 in the present embodiment, as illustrated in FIG. 2, is configured to execute various processes, such as the optic disc detection process (Step S5), the blood vessel detection process (Step S6), and the arteriovenous diameter ratio calculation process (Step S7). However, the PC 1 may execute only some of the processes described with reference to the foregoing embodiment.

For example, the PC 1 is configured to execute the arteriovenous diameter ratio detection process (Step S7) without executing the G-value luminance difference image acquisition process (Step S4), the optic disc detection process (Step S5), and the blood vessel detection process (Step S6). In this case, the PC 1 may identify the optic disc and a blood vessel by detecting the optic disc and the blood vessel by using another algorithm. The PC 1 may identify the optic disc and the blood vessel by acquiring, via a network and the like, data about the optic disc and the blood vessel that has been created by another device through processing of the fundus image. Namely, the PC 1 can execute the arteriovenous diameter ratio calculation process as long as the PC 1 can identify the optic disc and the blood vessel by some means.

The PC 1 may execute only the optic disc detection process (Step S5). For example, the PC 1 creates a 2D or 3D stereoscopic image by processing a plurality of fundus images with different parallaxes with reference to the optic disc position detected by the optic disc detection process. Further, the PC 1 may execute the blood vessel detection process (Step S6) described with reference to the foregoing embodiment for purposes other than for calculating the arteriovenous diameter ratio.

In the foregoing embodiment, processes for eliminating a segment, a blood vessel pair, and the like that are likely to be unwanted are implemented (such as in Step S81 to Step S83 in FIG. 14, and Step S113 to Step S115 and Step S117 in FIG. 16). However, the PC 1 may execute some and not all of the processes. Instead of eliminating some of the segments and blood vessel pairs that have been created, the process of creating the segments and blood vessel pairs may be implemented without creating the segments and blood vessel pairs that are likely to be unwanted. Thus, the concrete process method may be modified as needed.

In the foregoing embodiment, a blood vessel is detected by using the G-value image. However, the PC 1 may be configured to detect the blood vessel by using a fundus image other than the G-value image. For example, when a fundus image and the like obtained by fluorescein fundus angiography (FAG) is used, the accuracy of detection of the blood vessel can be increased.

The fundus image processing method described with reference to the foregoing embodiment is not limited to the PC 1 and may be implemented by other devices. For example, software (program) for causing a computer to implement a process implemented by the CPU 2 of the PC 1 may be supplied to a system or an apparatus via a network or various recording media. In this case a computer in the system or the apparatus (such as a CPU) reads the program and executes the process.

In the present embodiment, a program for carrying out the processes (fundus image processing program) may be recorded in a recording medium such as the ROM 3.

In this configuration, an arithmetic unit (CPU or micro processing unit (MPU)) of the information processing device reads the program recorded in the recording medium and executes the processes. Therefore, it can be said that the program itself realizes the processes.

As the above information processing device, in addition to a general computer (e.g., a workstation or personal computer), a function expansion board or function expansion unit that is attached to a computer can be used.

Moreover, the above program includes program codes (an executable program, an intermediate code program, a source program, and the like) of software that realizes the processes. The program may be used singly or in combination with another program (such as an operating system (OS)). Moreover, the program may be read from a recording medium, then recorded once in memory (such as RAM) in the device, and subsequently read again to be executed.

Moreover, a recording medium in which the program is recorded may be one that can be separated readily from the information processing device, or one that is fixed (attached) to the device. Furthermore, a recording medium may be one that is connected to the device as an external storage device.

A magnetic tape such as a video tape or cassette tape, a magnetic disk such as a floppy (registered trademark) disk, MiniDisc (MD), or hard disk, a magneto-optical disk such as an MO, an optical disc such as a compact disc (CD), digital versatile disc (DVD) or Blu-ray Disc (BD), a memory card such as an integrated circuit card (IC card) or optical card, a semiconductor memory such as a Mask ROM, erasable programmable read only memory (EPROM), electrically erasable programmable read-only memory (EEPROM), flash ROM, or USB memory, or the like can be applied as such a recording medium.

Moreover, a recording medium that is connected to the information processing device via networks (an intranet, the Internet, and the like) can be used. In this case, the information processing device acquires the program by downloading via a network. In other words, the above program may be acquired via a transmission medium (a medium holding the program in flux) such as a network (one that is connected to a wired or wireless channel). It is preferable that a program for download should previously be stored in the information processing device (or in a transmitting side device/receiving side device). Moreover, the above recording medium is a non-transitory (non-transitory) medium.

The technology according to the present disclosure may include the following first to tenth fundus image processing apparatuses and a first recording medium. Namely, the first fundus image processing apparatus is a fundus image processing apparatus that calculates the arteriovenous diameter ratio in the fundus of an examinee's eye by processing a fundus image of the examinee's eye, and that includes a processor, and a memory storing computer readable instructions, when executed by the processor, causing the fundus image processing apparatus to: identify the optic disc included in the fundus image; identify a blood vessel included in the fundus image; calculate an upper diameter ratio which is a diameter ratio of those of identified blood vessels that are positioned in a region above a height of the optic disc; and calculate a lower diameter ratio which is a diameter ratio of those of the identified blood vessels that are positioned in a region under the height of the optic disc.

The second fundus image processing apparatus is the first fundus image processing apparatus, wherein the computer readable instructions when executed by the processor causes the fundus image processing apparatus to: divide the blood vessel identified by the blood vessel identification unit into a plurality of segments by using at least a branching portion and an intersecting portion of the blood vessels as end points; determine one or a plurality of groups of a pair of two segments from the plurality of divided segments; and calculate the upper diameter ratio and the lower diameter ratio by calculating the diameter ratio of the segments in the determined pair.

The third fundus image processing apparatus is the second fundus image processing apparatus, wherein, when the plurality of groups of the pair is determined from each of the upper region and the lower region, the computer readable instructions when executed by the processor causes the fundus image processing apparatus to preferentially calculate the upper diameter ratio and the lower diameter ratio of the pair with a shorter distance between the segments.

The fourth fundus image processing apparatus is the third fundus image processing apparatus, wherein the computer readable instructions when executed by the processor causes the fundus image processing apparatus to: eliminate the pair of which a difference between the upper diameter ratio and the lower diameter ratio is equal to or greater than a first threshold value from the object for calculation of the upper diameter ratio and the lower diameter ratio; and calculate the upper diameter ratio and the lower diameter ratio of the pair of one or the plurality of groups of the pair of the plurality of determined groups of which a distance between the segments is short next to the eliminated pair.

The fifth fundus image processing apparatus is the second fundus image processing apparatus, wherein the computer readable instructions when executed by the processor causes the fundus image processing apparatus to determine the pair from those of the plurality of divided segments of which a length is equal to or greater than as second threshold value.

The sixth fundus image processing apparatus is the second fundus image processing apparatus, wherein the computer readable instructions when executed by the processor causes the fundus image processing apparatus to determine the pair from those of the plurality of divided segments of which a width is equal to or greater than a third threshold value.

The seventh fundus image processing apparatus is the second fundus image processing apparatus, wherein the computer readable instructions when executed by the processor causes the fundus image processing apparatus to determine the pair from those of the plurality of divided segments of which a distance from the optic disc is equal to or less than a fourth threshold value.

The eighth fundus image processing apparatus is the second fundus image processing apparatus, wherein the computer readable instructions when executed by the processor causes the fundus image processing apparatus to calculate the upper diameter ratio or the lower diameter ratio from the pair of which an angular difference of two of the plurality of divided segments is equal to or less than a fifth threshold value.

The ninth fundus image processing apparatus is the second fundus image processing apparatus, wherein the computer readable instructions when executed by the processor causes the fundus image processing apparatus to calculate the upper diameter ratio and the lower diameter ratio from the pair of the pairs of which a calculation result of the upper diameter ratio and the lower diameter ratio falls within an allowable range.

The tenth fundus image processing apparatus is the first fundus image processing apparatus, wherein the computer readable instructions when executed by the processor causes the fundus image processing apparatus to calculate an average value of the calculated upper diameter ratio and the lower diameter ratio.

The first record medium is a non-transitory computer readable recording medium and stores computer readable instructions, when executed by a processor, causing an image processing apparatus to: identify the optic disc included in a fundus image; identify a blood vessel included in the fundus image; calculate an upper diameter ratio which is a diameter ratio of those of identified blood vessels that are positioned in a region above a height of the optic disc; and calculate a lower diameter ratio which is as diameter ratio of those of the identified blood vessels that are positioned in a region under the height of the optic disc.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A fundus image processing apparatus that processes a fundus image of an examinee's eye, the fundus image processing apparatus comprising:

a processor; and a memory storing computer readable instructions, when executed by the processor, causing the fundus image processing apparatus to:

identify the optic disc included in the fundus image;

identify a blood vessel included in the fundus image;

calculate an upper diameter ratio which is a diameter ratio of those of the identified blood vessels that are positioned in a region above a height of the optic disc;

calculate a lower diameter ratio which is a diameter ratio of those of the identified blood vessels that are positioned in a region under the height of the optic disc; and calculate an arteriovenous diameter ratio in the fundus of the examinee's eye based on the upper diameter ratio and the lower diameter ratio.

2. The fundus image processing apparatus according to claim 1, wherein the computer readable instructions when executed by the processor causes the fundus image processing apparatus to:

divide the identified blood vessel into a plurality of segments with reference to a branching portion and an intersecting portion of the blood vessel as end points;

determine a pair of two of the plurality of segments; and calculate the upper diameter ratio and the lower diameter ratio by calculating a diameter ratio of the two segments of the pair.

3. The fundus image processing apparatus according to claim 2, wherein the computer readable instructions when executed by the processor causes the fundus image processing apparatus to:

determine a plurality of groups of the pair from each of a plurality of segments in the upper region and each of a plurality of segments in the lower region; and preferentially calculate the upper diameter ratio and the lower diameter ratio of the pair with a shorter interval between the segments.

4. The fundus image processing apparatus according to claim 3, wherein the computer readable instructions when executed by the processor causes the fundus image processing apparatus to:

eliminate the pair of which a difference between the upper diameter ratio and the lower diameter ratio is equal to or greater than a first threshold value from an object for calculation of the upper diameter ratio and the lower diameter ratio; and calculate the upper diameter ratio and the lower diameter ratio of the pair of one or a plurality of groups with a short segment interval.

5. The fundus image processing apparatus according to claim 2, wherein the computer readable instructions when executed by the processor causes the fundus image processing apparatus to determine the pair from the segments having a length equal to or greater that a second threshold value.

6. The fundus image processing apparatus according to claim 2, wherein the computer readable instructions when executed by the processor causes the fundus image processing apparatus to determine the pair from the segments having a width equal to or greater than a third threshold value.

7. The fundus image processing apparatus according to claim 2, wherein the computer readable instructions when executed b the processor causes the fundus image processing apparatus to determine the pair from the segments having a distance from the optic disc equal to or less than a fourth threshold value.

8. The fundus image processing apparatus according to claim 2, wherein the computer readable instructions when executed by the processor causes the fundus image processing apparatus to calculate the upper diameter ratio or the lower diameter ratio by using a pair having an angular difference of the two segments equal to or less than a fifth threshold value.

9. The fundus image processing apparatus according to claim 2, wherein the computer readable instructions when executed by the processor causes the fundus image processing apparatus to calculate the arteriovenous diameter ratio by using one of the pairs that has a calculation result of the upper diameter ratio and the lower diameter ratio which falls within an allowable range.

10. The fundus image processing apparatus according to claim 1, wherein the computer readable instructions when executed by the processor causes the fundus image processing apparatus to calculate an average value of the calculated upper diameter ratio and the lower diameter ratio as the arteriovenous diameter ratio.

11. A non-transitory computer readable recording medium storing computer readable instructions, when executed by the processor, causing an image processing apparatus to:

identify the optic disc included in the fundus image;

identify a blood vessel included in the fundus image;

calculate an upper diameter ratio which is a diameter ratio of those of identified the blood vessels that are positioned in a region above a height of the optic disc;

calculate a lower diameter ratio which is a diameter ratio of those of the identified blood vessels that are positioned in a region under the height of the optic disc; and calculate an arteriovenous diameter ratio in the fundus of the examinee's eye based on the upper diameter ratio and the lower diameter ratio.

12. A fundus image processing method for processing a fundus image of an examinee's eye, the fundus image processing method comprising:

identifying the optic disc included in the fundus image;

identifying a blood vessel included in the fundus image;

calculating an upper diameter ratio which is a diameter ratio of those of the identified blood vessels that are positioned in a region above a height of the optic disc;

calculate a lower diameter ratio which is a diameter ratio of those of the identified blood vessels that are positioned in a region under the height of the optic disc; and calculating an arteriovenous diameter ratio in the fundus of the examinee's eye based on the upper diameter ratio and the lower diameter ratio.

13. A non-transitory computer readable recording medium having recorded therein a fundus image processing program for causing a computer to execute the fundus image processing method according to claim 12.

* * * * *